(12) United States Patent
Solar et al.

(10) Patent No.: US 9,445,793 B2
(45) Date of Patent: *Sep. 20, 2016

(54) TRAJECTORY GUIDE, ACCESS PORT, AND FIDUCIAL MARKER ALIGNMENT

(71) Applicant: C2C Development, LLC, Melbourne, FL (US)

(72) Inventors: Matthew S. Solar, Indialantic, FL (US); Craig J. Pagan, West Melbourne, FL (US); Glenn D. Perry, Melbourne, FL (US); Anthony Adam-Henry Wittfeldt, Port Saint Lucie, FL (US)

(73) Assignee: C2C Development, LLC, Melbourne, FL (US)

(*) Notice: Subject to any disclaimer, the term of this patent is extended or adjusted under 35 U.S.C. 154(b) by 68 days.

This patent is subject to a terminal disclaimer.

(21) Appl. No.: 14/293,168

(22) Filed: Jun. 2, 2014

(65) Prior Publication Data

US 2014/0288578 A1 Sep. 25, 2014

Related U.S. Application Data

(63) Continuation of application No. 13/707,110, filed on Dec. 6, 2012, now Pat. No. 8,747,419, which is a continuation-in-part of application No. PCT/US2011/039963, filed on Jun. 10, 2011.

(60) Provisional application No. 61/353,251, filed on Jun. 10, 2010, provisional application No. 61/354,278, filed on Jun. 14, 2010.

(51) Int. Cl.
*A61B 19/00* (2006.01)
*A61B 17/00* (2006.01)
*A61B 17/34* (2006.01)

(52) U.S. Cl.
CPC ...... *A61B 17/00234* (2013.01); *A61B 17/3421* (2013.01); *A61B 2017/3407* (2013.01); *A61B 2034/2055* (2016.02); *A61B 2090/103* (2016.02)

(58) Field of Classification Search
CPC ............... A61B 19/201; A61B 2019/5483; A61B 19/5244; A61B 19/54; A61B 2019/208; A61B 2019/507; A61B 19/203; A61B 19/20; A61N 1/0539
See application file for complete search history.

(56) References Cited

U.S. PATENT DOCUMENTS

| 4,809,694 A | 3/1989 | Ferrara |
|---|---|---|
| 6,018,094 A | 1/2000 | Fox |

(Continued)

FOREIGN PATENT DOCUMENTS

| DE | 10029368 A1 | 12/2001 |
|---|---|---|
| EP | 2324790 A1 | 5/2011 |

(Continued)

OTHER PUBLICATIONS

U.S. Appl. No. 13/707,110, Examiner Interview Summary mailed Nov. 12, 2013, 3 pgs.

(Continued)

*Primary Examiner* — Katherine M Shi
(74) *Attorney, Agent, or Firm* — Schwegman Lundberg & Woessner, P.A.

(57) ABSTRACT

A trajectory guide for introducing an instrument into a human or animal subject is described. A guide stem can be removed in sections without disturbing the aligned instrument. An access port portion of the trajectory guide can be left in place, without disturbing trajectory alignment, and can allow overlying skin to be sutured closed. The access port can provide infusate delivery, such as using an injection port, catheter or the like. A fiducial marker arrangement can provide easy and accurate trajectory alignment, for use with the present trajectory guide, another trajectory guide, or without any trajectory guide.

21 Claims, 18 Drawing Sheets

(56) References Cited

U.S. PATENT DOCUMENTS

| | | | |
|---|---|---|---|
| 6,520,969 B2 | 2/2003 | Lambrecht et al. | |
| 6,529,765 B1 | 3/2003 | Franck et al. | |
| 6,902,569 B2 | 6/2005 | Parmer et al. | |
| 7,004,948 B1 | 2/2006 | Pianca et al. | |
| 7,204,840 B2 | 4/2007 | Skakoon et al. | |
| 7,815,651 B2 | 10/2010 | Skakoon et al. | |
| 8,747,419 B2 | 6/2014 | Solar et al. | |
| 2001/0003156 A1* | 6/2001 | Gill | A61B 19/201 606/130 |
| 2002/0049451 A1* | 4/2002 | Parmer | A61B 19/201 606/108 |
| 2005/0182420 A1* | 8/2005 | Schulte | A61N 1/0539 606/130 |
| 2009/0171184 A1 | 7/2009 | Jenkins et al. | |
| 2013/0096570 A1 | 4/2013 | Solar et al. | |

FOREIGN PATENT DOCUMENTS

| | | | |
|---|---|---|---|
| WO | WO-0178814 A1 | | 10/2001 |
| WO | WO 2009/047494 | * | 4/2009 |
| WO | WO-2009047494 A1 | | 4/2009 |
| WO | WO-2011156701 A2 | | 12/2011 |

OTHER PUBLICATIONS

U.S. Appl. No. 13/707,110, Non Final Office Action mailed Apr. 24, 2013, 16 pgs.

U.S. Appl. No. 13/707,110, Notice of Allowance mailed Jan. 30, 2014, 12 pgs.

U.S. Appl. No. 13/707,110, Response filed Oct. 24, 2013 to Non Final Office Action mailed Apr. 24, 2013, 24 pgs.

"Dedicated for minimally invasive stereotactic neurosurgery", [Online]. Retrieved from the Internet: <URL: http://www.elekta.com/healthcare-professionals/products/elekta-neuroscience/stereotactic-neurosurgery/leksell-stereotactic-system.html>, (Accessed Oct. 24, 2013), 1 pg.

International Application Serial No. PCT/US2011/039963, International Preliminary Report on Patentability mailed Dec. 20, 2012, 12 pgs.

International Application Serial No. PCT/US2011/039963, International Search Report mailed Mar. 13, 2012, 6 pgs.

International Application Serial No. PCT/US2011/039963, Invitation to Pay Additional Fees and Where Applicable, Protest Fee mailed Nov. 2, 2011, 7 pgs.

International Application Serial No. PCT/US2011/039963, Written Opinion mailed Mar. 13, 2012, 10 pgs.

* cited by examiner

TRAJECTORY GUIDE, ACCESS PORT, AND FIDUCIAL MARKER ALIGNMENT

CLAIM OF PRIORITY

This patent application is a continuation of U.S. patent application Ser. No. 13/707,110, filed on Dec. 6, 2012, which is a continuation-in-part of PCT/US2011/039963, filed on Jun. 10, 2011 (later published as WO 2011/156701A2), through which the present patent application also claims the benefit of priority to: (1) Matthew S. Solar et al. U.S. Provisional Patent Application Ser. No. 61/353,251, entitled "CRANIAL ACCESS PORT DEVICE AND METHOD," filed on Jun. 10, 2010; and (2) Matthew S. Solar et al. U.S. Provisional Patent Application Ser. No. 61/354,278, entitled "MRI TRAJECTORY GUIDE DEVICE AND METHOD," filed on Jun. 14, 2010, each of which is hereby incorporated by reference herein in its entirety, and the benefit of priority of each of which is hereby claimed.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2011, C2C Development, LLC, All Rights Reserved.

BACKGROUND

A diagnostic, therapeutic, or other interventional procedure on a human or animal subject may involve introducing an instrument toward a desired target location within the subject. For example, an interventional procedure on the subject's brain may involve drilling a burr hole in a subject's skull, mounting a trajectory guide on the subject's skull, and guiding an instrument (e.g., a catheter, a needle, a cannula, an electrode, or other device) to the desired target within the subject, such as by using pre-operative or live images from an imaging modality (e.g., MR, CT, PET, ultrasound, etc.) in an image-guided procedure. Accurate guidance is desirable, particularly for an interventional procedure on the brain, where millimeter or sub-millimeter accuracy of the instrument location may be desirable. Some illustrative examples of interventional procedures on the brain can include, but are not limited to, deep brain stimulation (DBS), infusate delivery (e.g., of a pharmaceutical, biological, or other substance), or microelectrode recording.

Ferrara U.S. Pat. No. 4,809,694 discloses a raised ball-and-socket trajectory guide, in which a deformable ball is located substantially above the burr hole of the skull. In Ferrara, an external thumbscrew can be used to deform the ball to retain an instrument within a ball passage through the deformable ball.

Parmer et al. U.S. Pat. No. 6,902,569 discloses a ball-and-socket trajectory guide with a split ball providing hemispherical sections that capture a relaxable stabilizer. When a guide stem is removed from the ball, the relaxable stabilizer relaxes to grip an instrument within a ball passage through the relaxable stabilizer. After adjusting the instrument trajectory by pivoting the ball, the ball is locked into position using a hexagonal-handled locking member (230) (see Parmer at FIG. 7A that protrudes substantially above the burr hole and the skull). The instrument is then inserted through the locked-in trajectory. The protruding hexagonal-handled locking member (230) is then removed, and a cap 310 is pressed or threaded into place to cover the ball. (See Parmer at col. 14, lines 22-38.)

Skakoon U.S. Pat. No. 7,204,840 and Skakoon U.S. Pat. No. 7,815,861 disclose examples of ball-and-socket trajectory guides that can be used in conjunction with peel-away sheaths. Skakoon U.S. Pat. No. 7,204,840 also shows an example of fiducial markers that can be attached to component associated with a trajectory guide apparatus. (See Skakoon U.S. Pat. No. 7,204,840 at FIG. 39.)

Jenkins U.S. Patent Publication No. 2007/0171184 discloses an example of a raised saddle trajectory guide that can be used in conjunction with a peel-away sheath. (See, e.g., Jenkins at FIG. 6c, ¶0067, ¶0073, ¶0076.)

OVERVIEW

The present inventors have recognized, among other things, that one general problem with certain trajectory guides, for example raised-saddle type trajectory guides, is that they protrude substantially above the burr hole, such that they cannot be left in place chronically after the instrument has been painstakingly delivered to the target in as accurate of a fashion as possible. Such protrusions are not only unappealing in appearance, they can risk injury to the subject in a chronic ambulatory setting, such as if bumped. Instead, such trajectory guides are removed after securing the instrument in place by some other means—but such removal and securing the instrument may itself perturb the location of the instrument.

The present inventors have also recognized that, while a lower-profile ball-and-socket trajectory guide may be used to deliver the instrument to the desired target, many such ball-and-socket trajectory guides still protrude substantially above the burr hole, such that they cannot be left in place chronically after the instrument has been painstakingly delivered to the target in as accurate of a fashion as possible, as explained above. The present inventors have recognized that, for example, a ball-and-socket trajectory guide like that shown in Parmer et al. U.S. Pat. No. 6,902,569, even if its ball-and-socket were placed substantially in the burr hole, still requires a hexagonal handled locking member (230) that protrudes substantially above the burr hole, which must be removed. However, such removal risks perturbing the accuracy of the carefully-placed instrument, even if it were to later be secured by some other means.

The present subject matter describes, among other things, a ball-and-socket trajectory guide in which the ball can be secured after trajectory alignment, such that the instrument can then be introduced through the ball along the aligned trajectory until it reaches the desired target, and such securing of the ball need not be later released during the procedure. Moreover, since the ball-and-socket and retaining member can be confined substantially within the burr hole, without protruding therefrom, the assembly can be left in place chronically for an ambulatory or other subject, such as by allowing skin to be sutured fully or partially closed above the assembly such as for improved appearance and decreased risk of infection, without creating the risk of bumping and injury from a substantial protrusion above the burr hole.

The present subject matter further describes a guide stem that can engage a ball passage to increase its effective bore length. In an example, the guide stem can be peeled apart or otherwise removed in sections with the instrument remaining in place, and such that the instrument can remain in place in the ball passage without being confined by the guide stem after the guide stem is removed. This can be particularly convenient if the instrument includes a proximal portion having a greater diameter than that of the instrument-guiding guide stem bore.

The present subject matter further describes a sealing cap with an injection port that can be used to cover the ball-and-socket in the burr hole, such as in a manner that can provide a fluid-retaining reservoir under the cap, which fluid can then be delivered to the target over an acute, extended, or chronic period of time, as desired.

The present subject matter further describes a first set of one or more user-visualizable or machine-visualizable, machine-imageable or other user-recognizable or machine-recognizable fiducial markers that can be provided and arranged to define a first plane that can be orthogonal to the trajectory. This can provide convenient image-guidance referencing, such as during alignment of the trajectory. The one or more fiducial markers defining the first plane orthogonal to the trajectory can define a first centroid on such first plane in a specified or determinable location. In an example, the one or more fiducial markers can be arranged such that the defined first centroid is at a location where the trajectory intersects the orthogonal first plane.

In a further example, a second set of one or more user-visualizable or machine-visualizable, machine-imageable or other user-recognizable or machine-recognizable fiducial markers can also be provided and arranged to define a second plane that can also be orthogonal to the trajectory, and spaced apart from the first plane. This can further provide convenient image-guidance referencing, such as during alignment of the trajectory. The one or more fiducial markers defining the second plane orthogonal to the trajectory can define a second centroid on such second plane in a specified or determinable location. In an example, the one or more fiducial markers can be arranged such that the defined second centroid is at a location where the trajectory intersects the orthogonal second plane (e.g., such as together with the first centroid being at a location where the trajectory intersects the orthogonal first plane).

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present subject matter is described herein with particular emphasis toward an example in the general field of medicine relating to the introduction, placement, or stabilization of one or more devices in the brain, such as to treat a tumor or another neurological disorder. The present subject matter can help improve at least two key elements of this procedure: (1) precise and accurate instrument trajectory guidance, and (2) securing the delivered device, such as to permit short term use, long term use, or both.

In an example, the present subject matter can include a cranial access port or other trajectory guide apparatus or method, such as for the delivery and placement of a device into a human body, such as into the skull, in particular. The cranial access port device can be used with one or more other devices or instruments that can benefit from precise and accurate introducing, placing, and securing within the brain, such as, for an illustrative example, a catheter for infusing material into or draining material out of the body.

Figure 1:
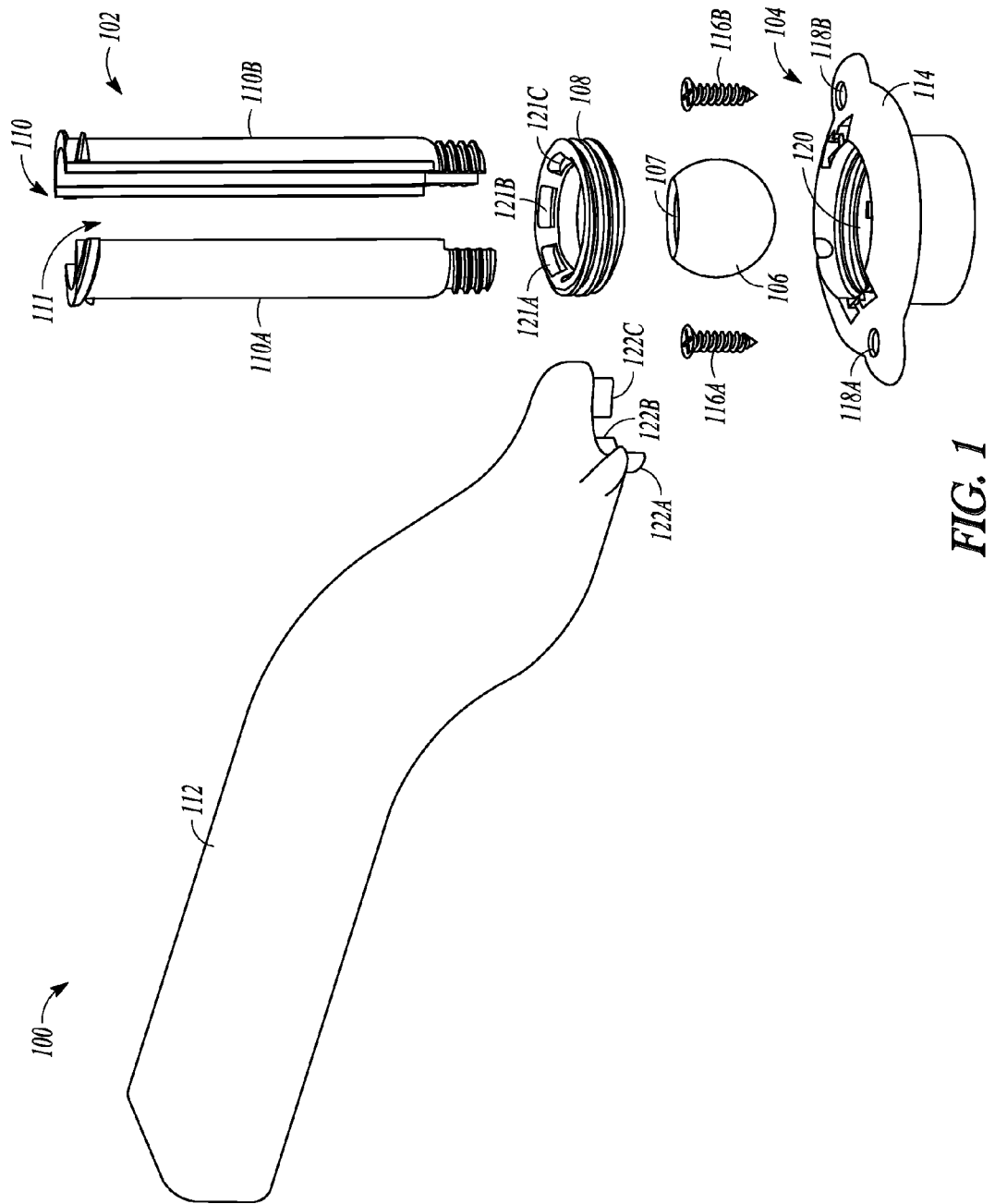
FIG. 1 shows an example of an exploded view of certain portions of a system that can include a trajectory guide apparatus and other components, which can be provided therewith.

FIG. 1 shows an example of an exploded view of certain portions of a system 100 that can include a trajectory guide apparatus 102 and one or more other components, which can be provided therewith, such as in the form of a pre-packaged or other kit, such as within a sealed sterilized package, which can be accompanied by instructions for use (IFUs). In an example, the trajectory guide apparatus 102 can include a base 104, a spherical or other pivotable ball 106, and a ball-locking ring or other retainer 108. The combination of the base 104, the ball 106, and the retainer 108 can be sized, shaped, or otherwise configured to be located substantially within a burr hole that has been drilled into a subject's skull, without substantially protruding above such burr hole. (A typical dimension for a burr hole drilled into the subject's skull is 14 millimeters in diameter.) This can help allow chronic placement of the combination of the base 104, the ball 106, and the retainer 108, such as to allow overlying skin to be sutured partially or completely shut, which can help improve appearance or reduce the risk of infection, while avoiding or reducing the risk of bumping a protruding component, which could cause injury to the subject to which such a protruding component is mounted.

The trajectory guide apparatus 102 can also include a removable guide stem 110, such as can provide a bore 111 extending longitudinally between proximal and distal ends of the guide stem 110. The guide stem 110 can engage the ball 106, such as threadably, snap-in, or otherwise, such that the bore 111 of the guide stem 110 can be aligned concentric to a ball passage 107 that can extend through the ball 106, such as between proximal and distal ends of the ball 106. The ball passage 107, alone or in combination with the bore 111 of the guide stem 110, can establish a longitudinal trajectory concentric thereto, along which an instrument can be delivered to a desired target. The desired target can be located within the subject's skull. The desired target can be located at a shallow depth directly below the skull surface above the cortex (e.g., zero depth) or the desired target can be located in deep brain structures at the base of the skull (e.g., at depths of 15 cm-20 cm), or the desired target can be located anywhere therebetween. The guide stem 110 can protrude above the burr hole, but the guide stem 110 can be removed from more distal components of the trajectory guide 102. These more distal components of the trajectory guide 102 can be left in place without substantial protrusion above the burr hole. In an example, the guide stem 110 can be removed in peel-away, peel-apart, twist-apart, break-apart, or other sections 110A-B, as explained further below. In an example, the system 100 or kit can include a wrench or other tool 112, such as having one or more male or female or other engageable features configured for engaging one or more corresponding female or male or other engageable features of the retainer 108. The tool 112 can be used to secure the retainer 108 to the base 104, such as to lock the ball 106 in a desired pivoting position. This can hold a desired trajectory constant, such as aligned toward a desired target within the subject.

In an example, the base 104 can include or be coupled to an optional low-profile flange 114. The low-profile flange 114 can be sized, shaped, or otherwise configured to extend at least partially about the burr hole, including slightly above a plane defined by the surface of the burr hole. This can help to locate the base 104 substantially within the burr hole (e.g., except for the low-profile flange 114). In an example, the flange 114 (including any low-profile cap placed to cover over a receptacle defined by the flange 114) can provide a low enough profile, such as less than or equal to 5 millimeters above the outer surface of the skull, so as to be capable of allowing overlying skin to be sutured closed over the flange 114. This can help permit an access port portion of the trajectory guide 102, e.g., formed by a combination of the base 104, the flange 114, the ball 106 and the retainer 108 (after the guide stem 110 has been removed) to be left in place chronically, such as subcutaneously, and can help reduce or avoid the risk of injury from a protrusion being bumped, or can help improve appearance or reduce the risk of infection. The flange 114 can be secured to the skull, such as by one or more bone screws 116A-B or other fasteners or an adhesive. The bone screws 116A-B can be passed through respective holes 118A-B in the flange 114 and screwed into the skull, thereby securing the flange 114 and the base 104 in place.

The flange 114 is not required. In an example, the low-profile flange 114 can be omitted, such as in an example in which the base 104 is provided with outer circumferential threads that can permit the base 104 to be threaded into the bony structure of the skull, such as to secure the base 104 to the skull. The outer circumferential threads are also not required. Another fixation mechanism or technique can additionally or alternatively be provided to secure the base 104 to the skull, such as with or without the flange 114. In an example, an expansion element can be provided such as to expand an expandable portion of the base 104 to securely fit within the burr hole in the skull, such as using one or any of a number of expansion elements such as can be used in certain drywall mounts or like applications that can involve outward expansion.

The base 104 can include a socket 120 therein. The socket 120 can be sized, shaped, or otherwise configured to be located within (including beneath) the burr hole. The socket 120 can be sized, shaped, or otherwise configured to allow movement of the ball 106, such as pivoting. This can permit aiming the concentric trajectory of the ball passage 107 toward a desired target, such as within the subject's skull. The ball 106 can then be securely locked into place. This can hold the aimed trajectory constant, and can be accomplished such as by using the retainer 108. In an example, the retainer 108 can include one or more engageable features 121A-C (e.g., male, female, or other) such as that do not protrude above a tangential plane defined by the top-most surface of the low-profile flange 114 or that of a similarly low-profile cap that can be placed over a receptacle provided by the base 104. This can help permit overlying skin to be sutured closed over the flange 114. As discussed above, this can help permit the access port portion of the trajectory guide 102, formed by the combination of the base 104, the optional flange 114, the ball 106, and the retainer 108, to be left in place chronically, such as subcutaneously, and can help reduce or avoid the risk of injury from a more substantial protrusion being bumped, as well as improving appearance or reducing the risk of infection. In the illustrative example of FIG. 1, such engageable features 121A-C of the retainer 108 can include one or more receptacles 121. The receptacles 121 can be located or distributed about or near a circumferential periphery of the retainer 108. The receptacles 121 can be engaged by mating protrusions 122 on the tool 112, in an example. In this example, turning the retainer 108 using the tool 112 threads the retainer 108 onto the base 104. In this manner, the retainer 108 can be tightened down onto the base 104. This can lock the ball 106 in place to hold constant the trajectory provided by the ball-passage 107, such as after the trajectory has been aligned toward a desired target within the subject beyond the base 104. The secured ball 106 can later receive a diagnostic, therapeutic, or other instrument through the ball passage 107, such as for delivery or retention of the instrument along the locked aligned trajectory to the desired target.

Figure 2:
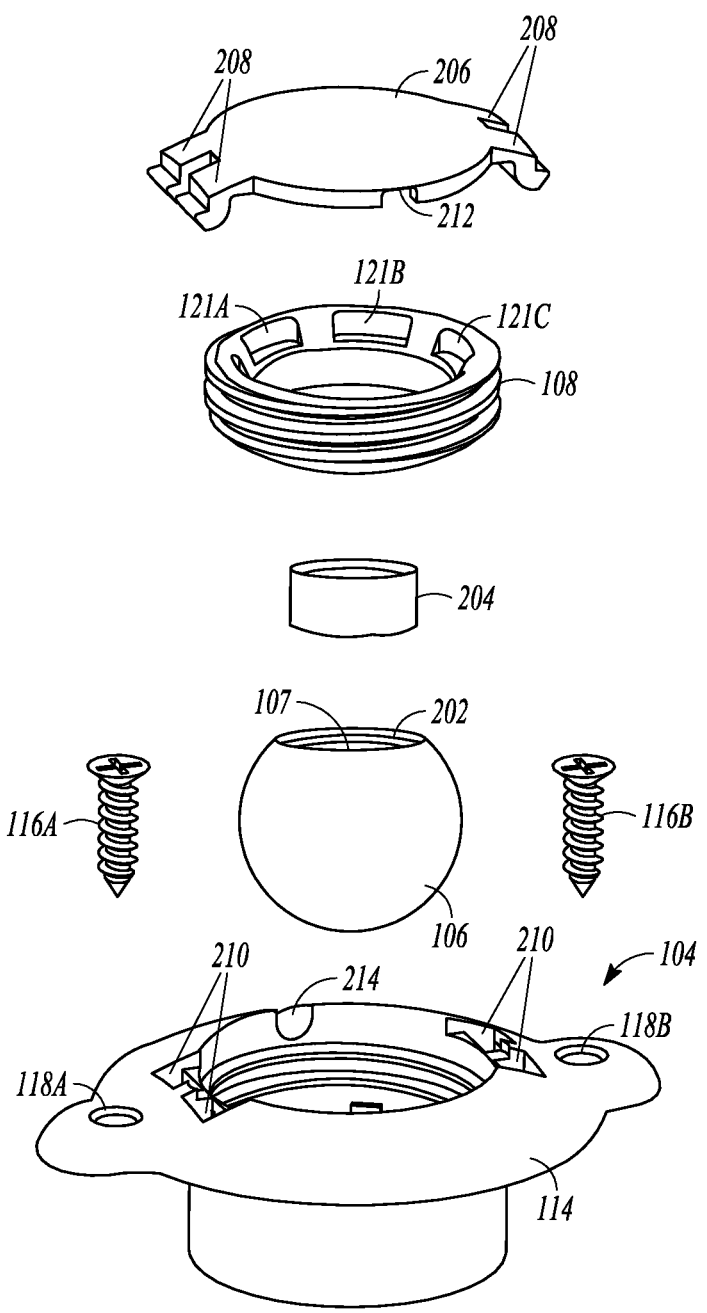
FIG. 2 shows an example of another exploded view of certain portions of an example of the system including portions of the trajectory guide apparatus, where the removable guide stem has been removed from more distal access port components of the trajectory guide apparatus.

FIG. 2 shows an example of another exploded view of certain portions of the system 100 including portions of the trajectory guide apparatus 102. In the illustrative example of FIG. 2, the removable guide stem 110 has been removed from the more distal access port components of the trajectory guide apparatus 102. Such removal of the guide stem 110 can, in an example, include unthreading an outer thread, extending (e.g., externally) about a distal circumferential portion of the guide stem 110, from an inner thread 202, extending (e.g., internally) about a proximal circumferential portion of the ball passage 107.

After the guide stem 110 has been removed, it may be desirable to reduce or avoid risk of the inner thread 202 of the ball passage 107 chafing or otherwise damaging or affecting the instrument remaining at least partially within the ball passage 107. Therefore, after unthreading the guide stem 110 to remove it from the ball passage 107, a cylindrical or other thread cover spacer 204 can be inserted into the ball passage 107. The spacer 204 can be used to cover the thread 202 or to provide an interior through-lumen that can present a substantially smooth interior surface to a portion of the instrument that is located within the ball passage 107. In an example, the spacer 204 can provide a cylinder with a substantially smooth surfaced lumen therethrough. In an example, an outer surface of the cylindrical spacer 204 can include a thread. This can allow the spacer 204 to be threaded onto the inner thread 202 of the ball passage. In an example, the outer surface of the cylindrical spacer 204 can be ribbed. This can allow the spacer 204 to be pressed-fitted onto the inner thread 202 of the ball passage 107. In an example, the outer surface of the cylindrical spacer 204 can be smooth, such as where the cylindrical spacer 204 is to be held in place using a portion of the retainer 108. In an example, the cylindrical spacer 204 can be delivered to the ball passage 107 by introducing it over the instrument through the ball passage 107, such as by passing the instrument through the lumen of the spacer 204, and then passing the cylindrical spacer 204 over the instrument. In an example, a proximal edge portion of the lumen of the cylindrical spacer 204 can similarly taper outward so as not to present an abrupt edge to an instrument exiting the proximal end of the ball passage 107. The spacer 204 can be helpful to address potential chafing, etc., of the instrument by the present trajectory guide apparatus 102, but it can also be used in conjunction with any other ball-and-socket or other trajectory guide apparatus or other device in which an instrument can be left in place acutely or chronically against one or more threads in a passage through which the instrument passes.

The example of FIG. 2 also illustrates an example of a low-profile cap 206. The low-profile cap 206 can be placed substantially within the flange 114, in an example. This can include snap-fitting feet 208 (such as can extend laterally outward from the cap 206) into corresponding snap-fit feet-retaining shoes 210 that can be formed into the flange 114, or into the base 104 (such as where the flange 114 is omitted). The cap 206 can have a low profile, such as described above with respect to the low-profile flange, such that overlying skin can be sutured closed over the flange 114 and over the cap 206. As discussed above, this can help permit the access port formed by the combination of the base 104, the optional flange 114, the ball 106 and the retainer 108 to be left in place chronically, such as subcutaneously.

This can help reduce or avoid the risk of injury from a substantial protrusion being bumped, such as in a chronic setting by an ambulatory subject. The cap 206 can have enough clearance below to allow the retainer 108 and the ball 106 to be operatively contained within the base 104 under the cap 206, which can be made of a clear material to allow visualization of these underlying components. In an example, the cap 206 can include or be made of a material that can seal against the flange 114 or the base 104. This can help retain fluid in a "reservoir" under the cap 206 and within the base 104. In an example the reservoir can include or be coupled to a micromechanical, electrokinetic, or other active or passive pump, such as for pumping or controlling delivery of the flowable substance to the desired target. For example, a passive pump can be included, such as to provide the reservoir, or coupled in fluid communication with the reservoir. The passive pump can include an at least partially elastic chamber, such as a bellows. The bellows can be filled with fluid, such as can cause the bellows to expand. As the bellows relaxes, it can provide a desired amount of positive pressure to urge infusate from the reservoir toward the target site.

In an example, the cap 206 can include an infusion or drainage or other port (e.g., a membrane, a valve, or the like). In an example, the port can be configured such that a flowable infusate can be injected or otherwise delivered through the port, such as using a syringe, an infusion pump, or other device. The port can be located at the center of the cap 206, or elsewhere. In an example, the cap 206 can include an instrument exit portal 214 to allow an instrument to exit (e.g., laterally) from under the cap 206. Such exiting can be either via the instrument exit portal 212 alone, or via the instrument exit portal 212 in the cap 206 in combination with an instrument exit portal 214 in the flange 114, which can be configured to align with the instrument exit portal 212 in the cap 206. In an example, one or both of these instrument exit portals 212, 214 can be configured to grip the instrument passed therethrough, such as to immobilize or stabilize it. In an example, one or both of these instrument exit portals 212, 214 can be configured to seal against the instrument exiting therethrough, such as to retain a flowable infusate under the cap 206.

Figure 3A:
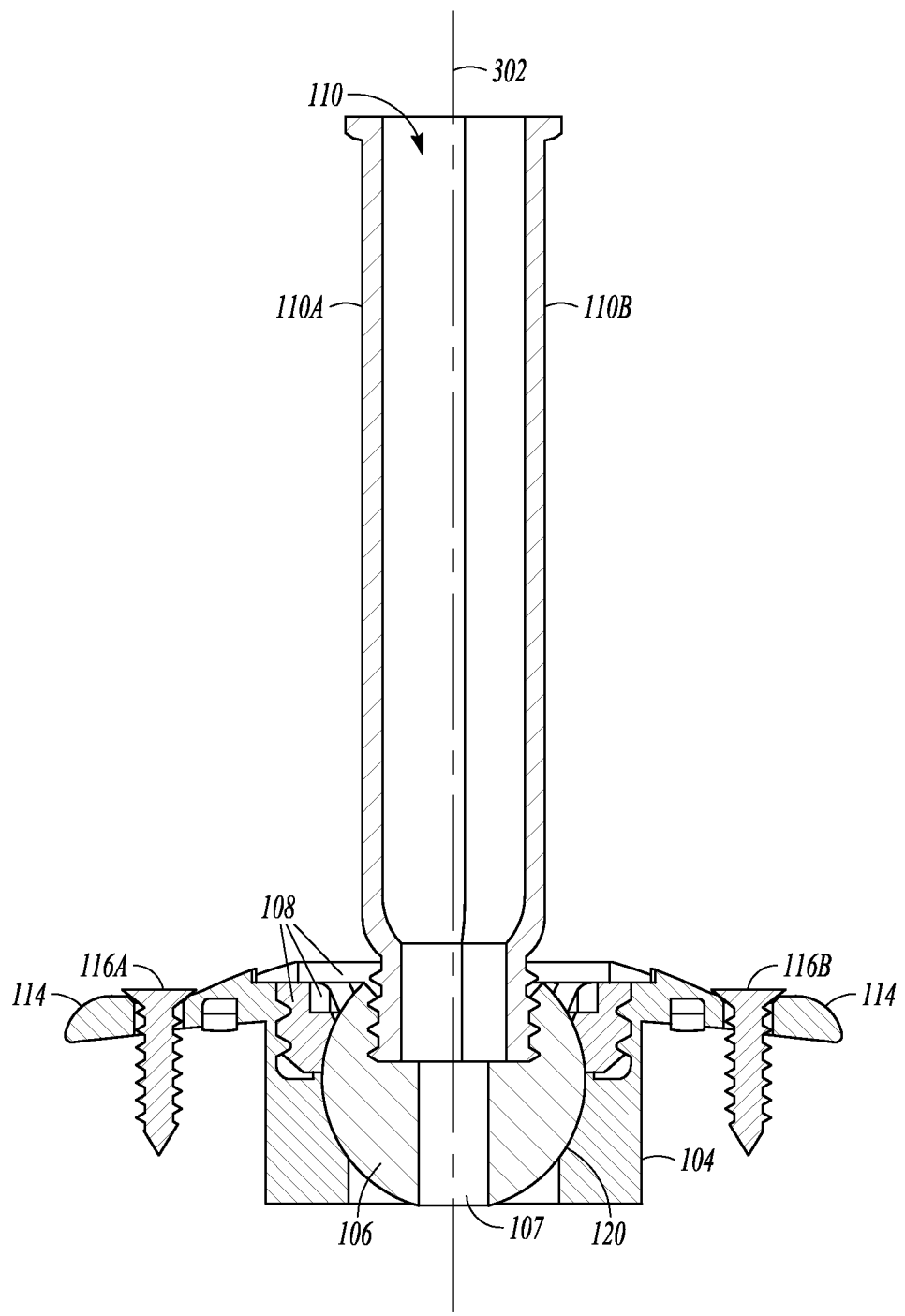
FIGS. 3A-3B show examples of respective cross-sectional views of an example of portions of the trajectory guide apparatus, in which the guide stem has been threaded into engagement with the ball passage of the ball.
Figure 3B:
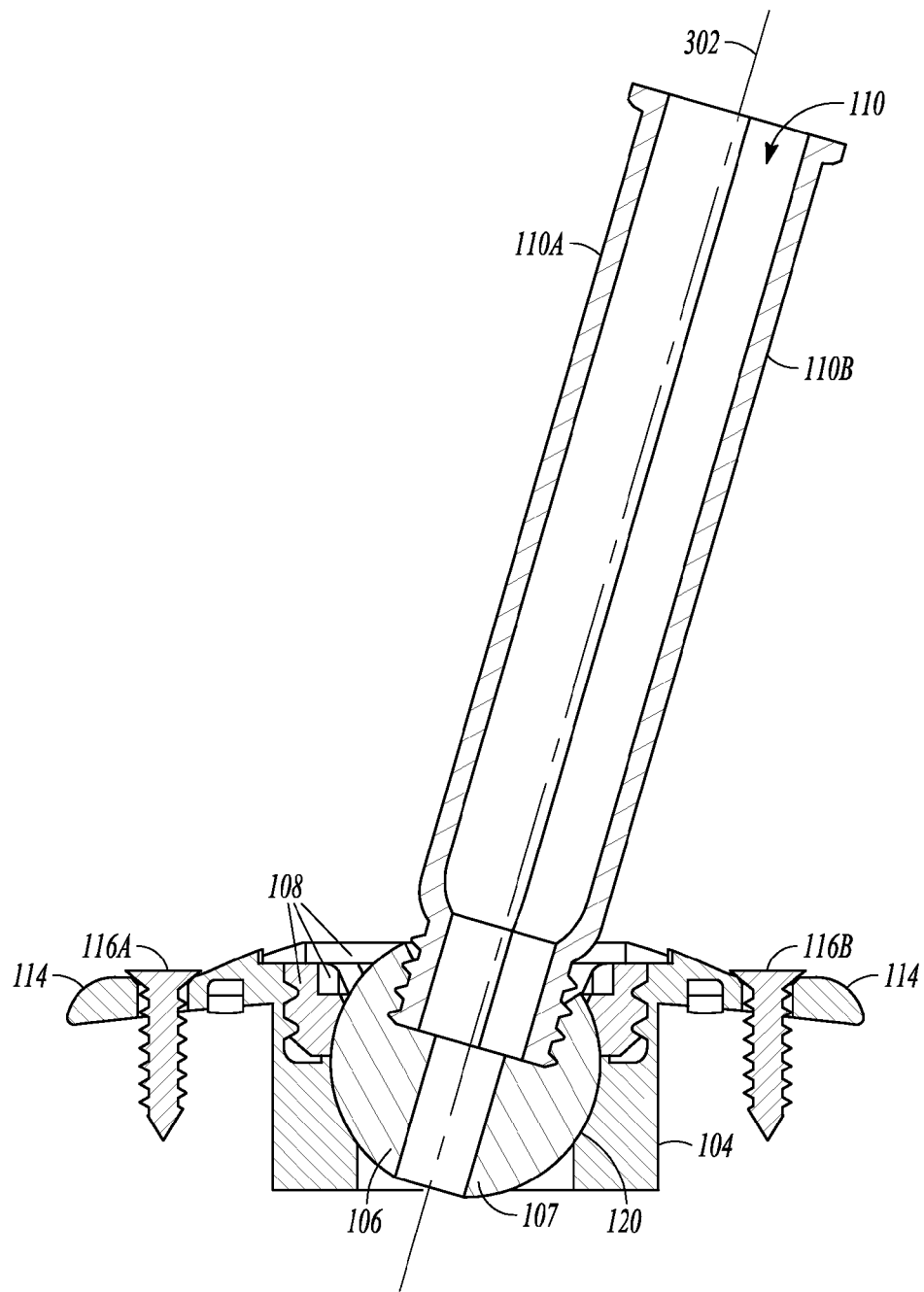

FIGS. 3A-B show examples of respective cross-sectional views of an example of portions of the trajectory guide apparatus 102, in which the guide stem 110 has been threaded into engagement with the ball passage 107 of the ball 106. The base 104 can be sized, shaped, or otherwise configured to include a socket 120 portion into which the ball 106 is seated, such as with a central pivot point of the ball 106 located below the surface of the skull. The socket 120 can be shaped to allow smooth pivoting of the ball 106 with respect to the socket 120. This can permit pivoting the ball 106, such as to obtain a desired alignment of the trajectory 302 toward a desired target within the skull. The retainer 108 can be threaded into the base 104, such as to securely lock the ball 106 down against the socket 120 portion of the base 104, such as to hold constant a desired trajectory 302. FIG. 3A shows an example in which the guide stem 110 can be vertically aligned with respect to the base 104, e.g., substantially parallel to an axis extending concentrically through the burr hole orthogonal to the skull. The retainer 108 can lock the ball 106 into this orientation. FIG. 3B shows an example in which the ball 106 can be pivoted with respect to the socket 120, such that the guide stem 110 can be aligned at an angle with respect to the axis extending concentrically through the burr hole orthogonal to the skull. The retainer 108 can lock the ball 106 into this orientation.

Figure 4A:
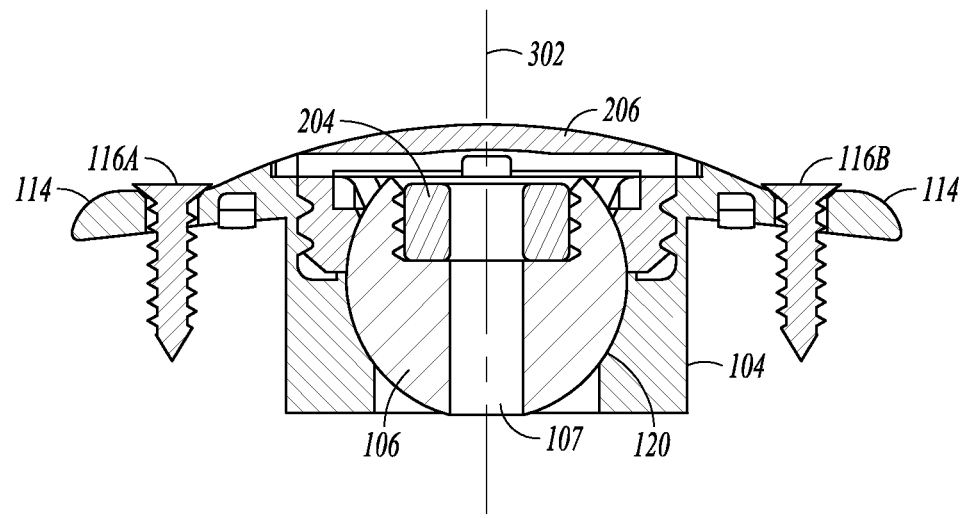
FIGS. 4A-B show examples of respective cross-sectional views of an example of portions of the trajectory guide apparatus, in which the guide stem has been removed, an optional thread covering spacer, has been inserted, and a cap has been introduced.
Figure 4B:
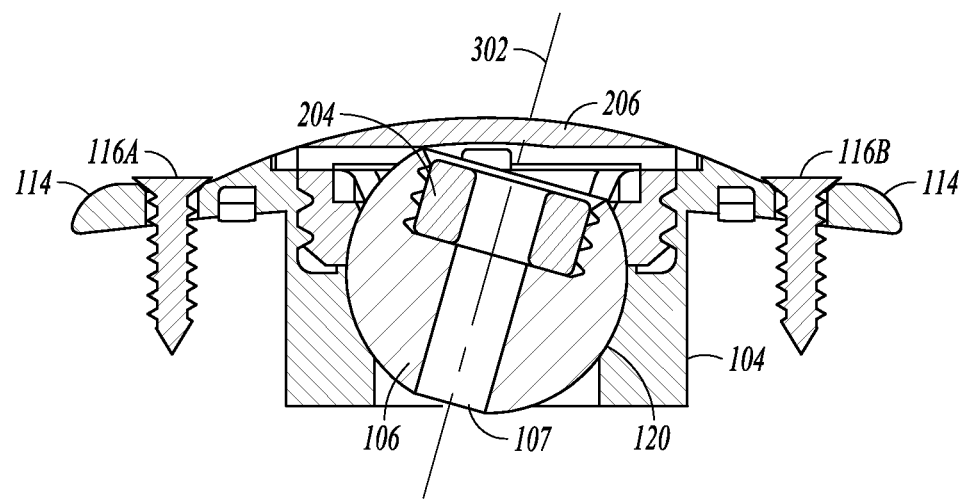

FIGS. 4A-B show examples of respective cross-sectional views of an example of portions of the trajectory guide apparatus 102, in which the guide stem 110 has been removed from engagement with the ball passage 107 of the ball 106. An optional thread covering spacer 204 has been inserted into a proximal portion of the ball passage 107 of the ball 106. A cap 207 has been snap-fitted or otherwise engaged into the flange 114 or the base 104. FIG. 4A shows an example in which the guide stem 110 can be vertically aligned with respect to the base 104, e.g., substantially parallel to an axis extending concentrically through the burr hole orthogonal to the skull. The retainer 108 can lock the ball 106 into this orientation. FIG. 4B shows an example in which the ball 106 can be pivoted with respect to the socket 120, such that the guide stem 110 can be aligned at an angle with respect to the axis extending concentrically through the burr hole orthogonal to the skull. The retainer 108 can lock the ball 106 into this orientation.

Figure 5:
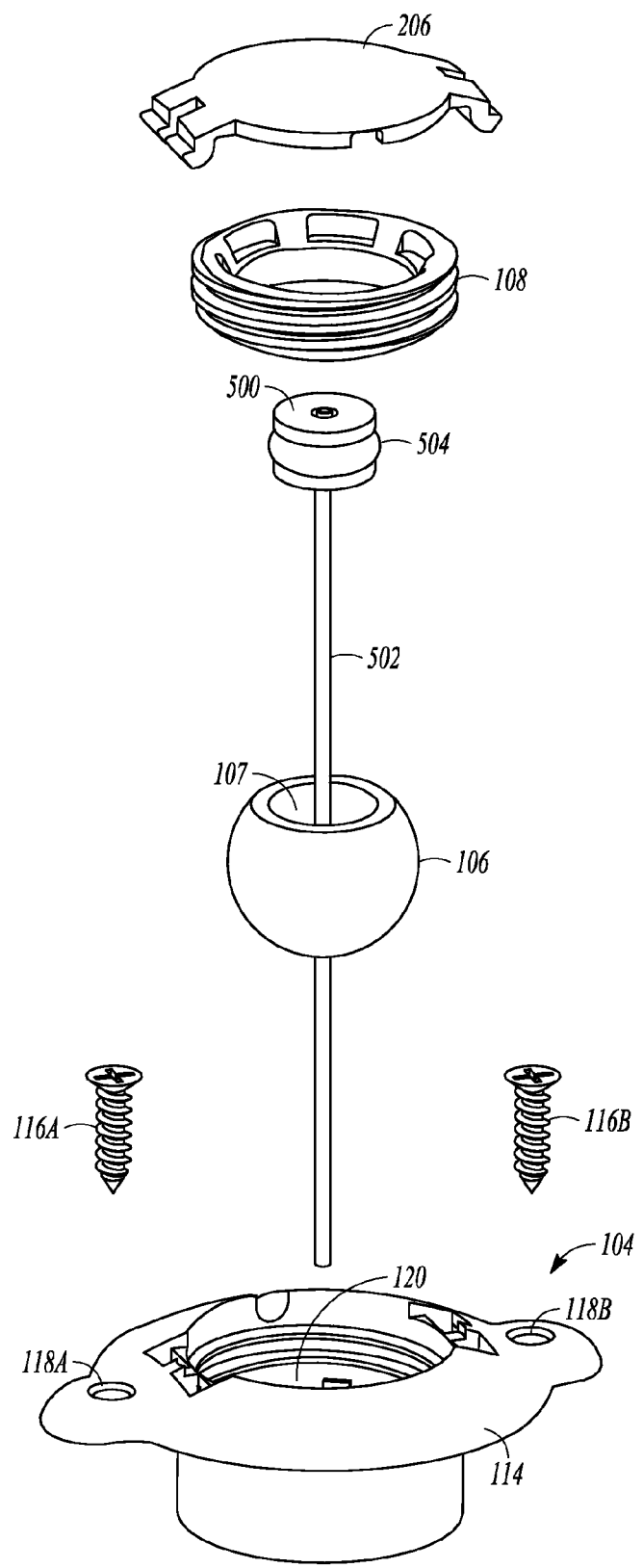
FIG. 5 shows an exploded view of portions of an example of the trajectory guide apparatus in which an instrument can be disposed along the trajectory.

FIG. 5 shows an exploded view of portions of an example of the trajectory guide apparatus 102 in which the instrument can include a rigid or other cannula 502, such as can be disposed along the trajectory 302. A distal end of the cannula 502 can be positioned at or near a desired shallow, deep, or other target within the skull. A proximal end of the cannula 502 can be received in a hub 500, such as within a central lumen of the hub 500. In an example, the hub 500 can seal against or otherwise engage a portion of the ball 106, such as within the ball passage 107. In an example, the hub 500 can seal against or otherwise frictionally engage an inner circumference of the ball passage 107. This can inhibit longitudinal movement of the hub 500 within the ball passage 107. Additionally or alternatively, this can seal against, or prevent fluid flow between the hub 500 and the inner circumference of the ball passage 107. In an example, the hub 500 can include or be coupled to an O-ring 504 or other seal extending about an outer circumference of the hub 500, such as to provide the sealing or other frictional engagement described above. In an example, the hub 500 can include a compliant stopper-like component, such that no separate O-ring 504 or seal is needed to provide the sealing or other frictional engagement. In an example, the cannula 502 itself can directly seal against or otherwise engage the inner circumference of the ball passage 107, such as where sealing or other frictional engagement is not needed, for example, if a nail-head-like or other stop of the cannula 502 comes to rest upon a proximal end of the ball 106. In an example, the cap 206, the optional flange 114, and portions within the base above the hub 500 can form a reservoir, such as for storing a flowable substance that can then be delivered to the desired target location, such as via the cannula 502.

Figure 6A:
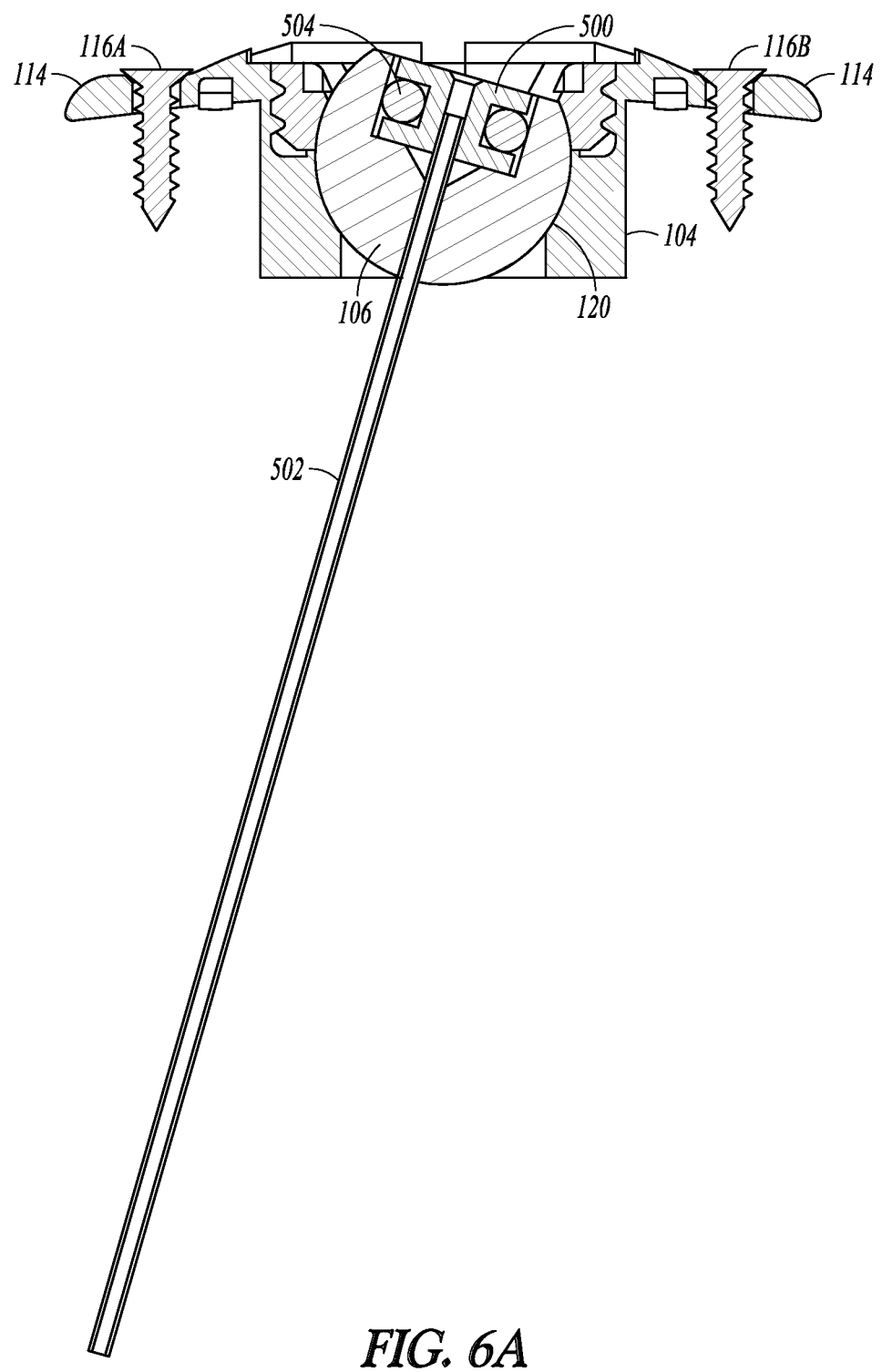
FIGS. 6A-B show cross-sectional views of an example of portions of the trajectory guide, respectively showing vertically and obliquely aligned instruments.
Figure 6B:
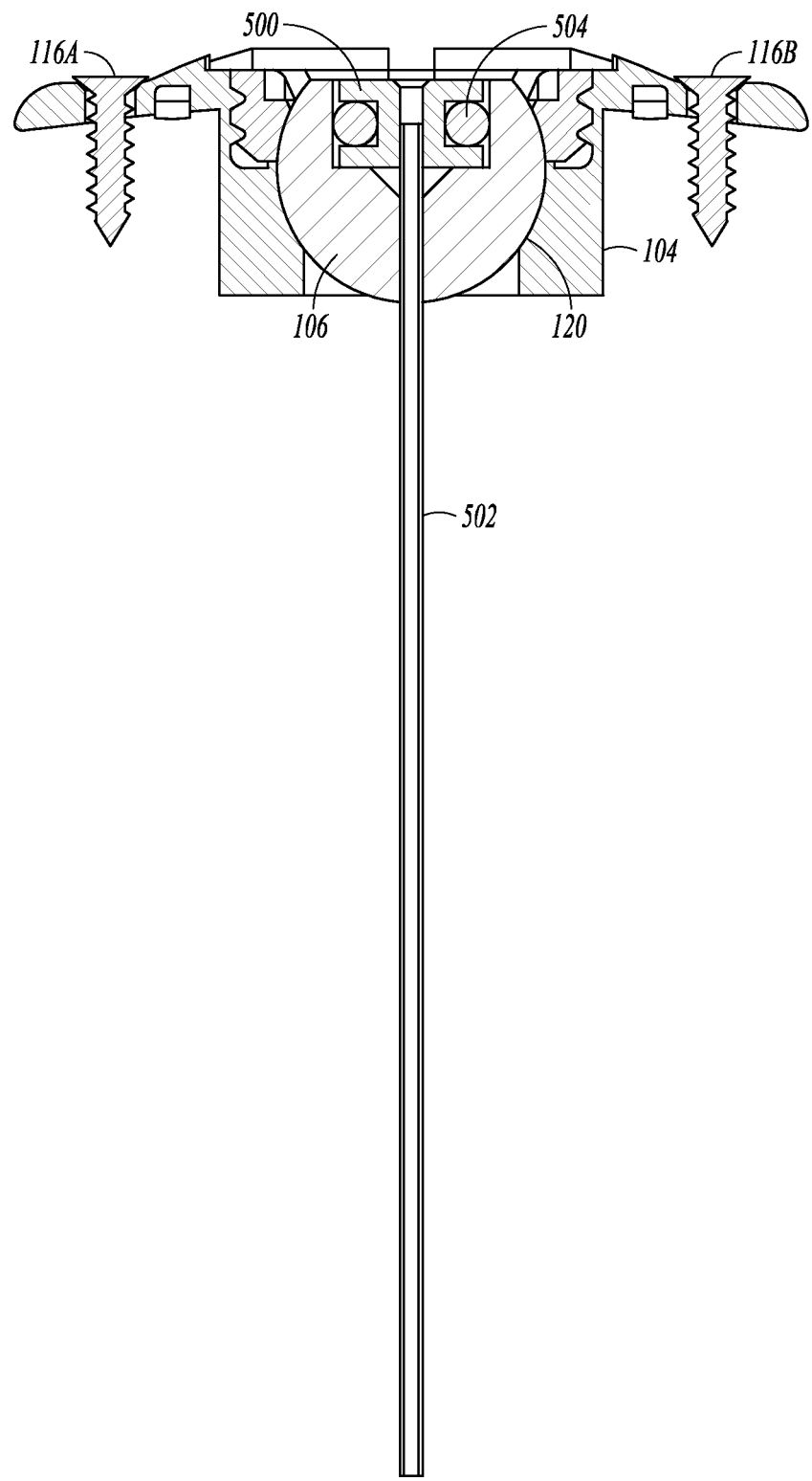

FIGS. 6A-B show cross-sectional views of an example of portions of the trajectory guide 102, respectively showing vertically and obliquely aligned cannulas 502, extending distally into the subject's skull from a proximal end of the cannula 502 that is engaged within the ball passage 107 of a ball 106 in a socket 120 of a base 104, such as sealingly or frictionally via the hub 500 or a component associated therewith, such as the O-ring 504 or other seal or brake.

Figure 7:
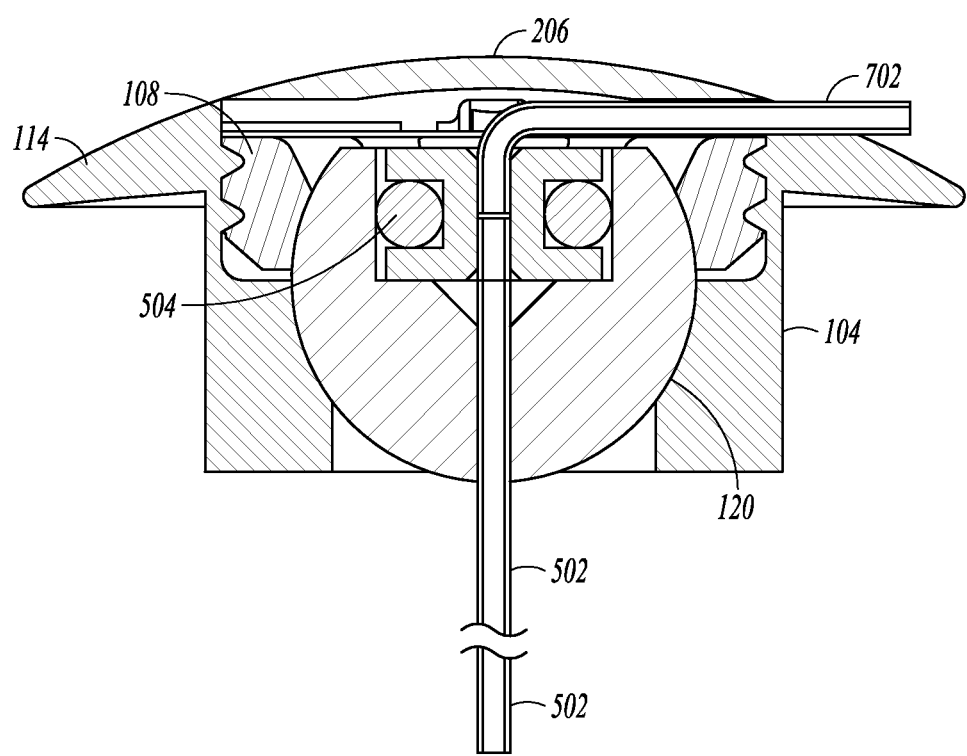
FIG. 7 shows a cross-sectional view of an example of portions of the trajectory guide, in which a rigid vertical cannula can be coupled with a flexible laterally-exiting catheter.

FIG. 7 shows a cross-sectional view of an example of portions of the trajectory guide 102, in which the rigid vertical cannula 502 can be coupled (e.g., in fluid communication) with a flexible laterally-exiting catheter 702. In this way, the lateral catheter 702 can be easily connected to or disconnected from the cannula 502, such as without disturbing the intracranial cannula 502 or the access port portion of the trajectory guide 102 to which the intracranial cannula 502 is secured. In an example, the lateral catheter 702 can help facilitate both connection to or removal from the intracranial cannula 502, such as at some time after the procedure in which the access port components of the trajectory guide 102 have been installed onto the subject. For example, it may be desirable to allow the associated installation incision to heal for some period of time before connecting the lateral extension line provided by the lateral catheter 702, or it may be desirable to "yank" out or otherwise remove the lateral extension catheter 702 without disturbing the intracranial cannula 502.

Figure 11:
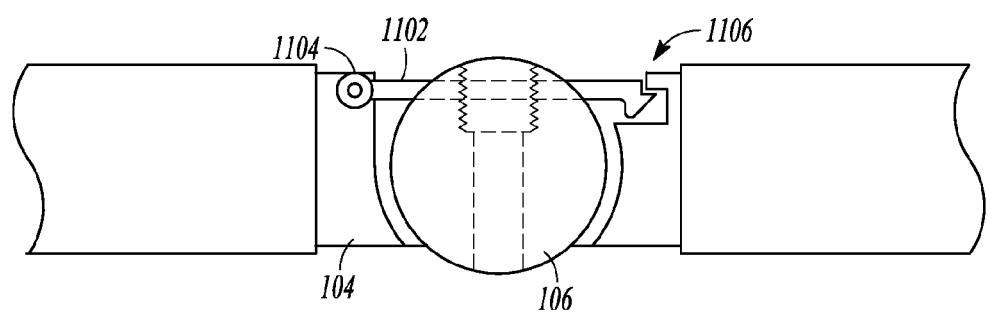
FIG. 11 shows an example of portion of the trajectory guide apparatus in which the retainer need not include threads.

FIG. 11 shows an example of portion of the trajectory guide apparatus 102 in which the retainer 108 need not include threads. In an example, the retainer 108 can include a retainer ring 1102 that can be seated upon the ball 106 such as to secure the ball 106 in place such as with the ball passage aligned to maintain a desired trajectory. In an example, the retainer ring 1102 can include a pinned or other hinge 1104 that can couple the retainer ring 1102 directly or indirectly to the base 104. The hinge 1104 can be located on one side of the retainer ring 1102, such that the retainer ring 1102 and the hinge 1104 can be configured in a manner similar to that of a hinged toilet seat. The other side of the retainer ring 1102 can include a fixation mechanism 1106 that can be configured to secure the retainer ring 1102, such as to press firmly against the ball 106 to hold the ball 106 in place and to inhibit pivoting by the ball 106. The fixation mechanism 1106 can include a male or female or other snap-fitting feature such as can be user-engaged directly or indirectly to the base 104, or can include a screw or any other fastener. The retainer ring 1102 can be configured such that when the fixation mechanism 1106 is engaged to the base 104, the retainer ring 1102 can be located substantially within the burr hole, such as to allow optional placement of the overlying cap 206, and such as to allow overlying skin to be sutured partially or fully closed, as desired, such as described above.

Figure 12:
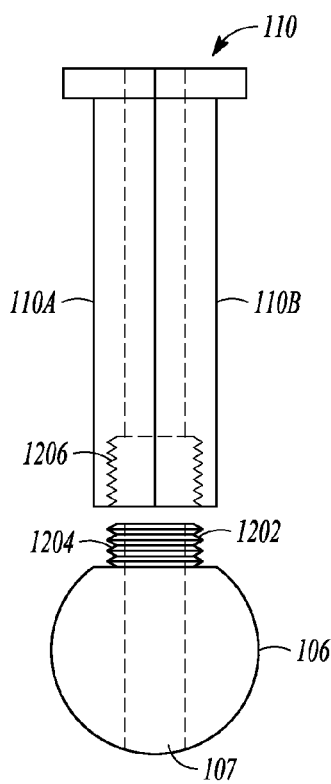
FIG. 12 shows an example in which the ball can include an external protrusion, such as a threaded or other post, to which the guide stem can be user-engaged or user-mounted.

FIG. 12 shows an example in which the ball 106 can include an external protrusion, such as a threaded or other post 1202, to which the guide stem 110 can be user-engaged or user-mounted. In an example, the post 1202 can include one or more threads, such as external threads 1204 extending about the circumferential periphery of the post 1202 to which corresponding internal threads 1206 or one or more other engageable features within an internal distal portion of the guide stem 110 can be threaded or otherwise engaged. The example shown in FIG. 12 can avoid needing internal threads within the ball passage 107 which, as explained above, can chafe against an instrument passing through the ball passage 107. This, in turn, can avoid any need for the optional cylindrical spacer 204 described above. The protrusion need not include a post 1202, but can include a ring, a lip, or other external feature of the ball 106. Engagement of the guide stem 110 to such post 1202 or other protrusion need not include threading, but can instead be via snap-fitting or another engagement mechanism or technique than can be performed by the user.

Figure 13:
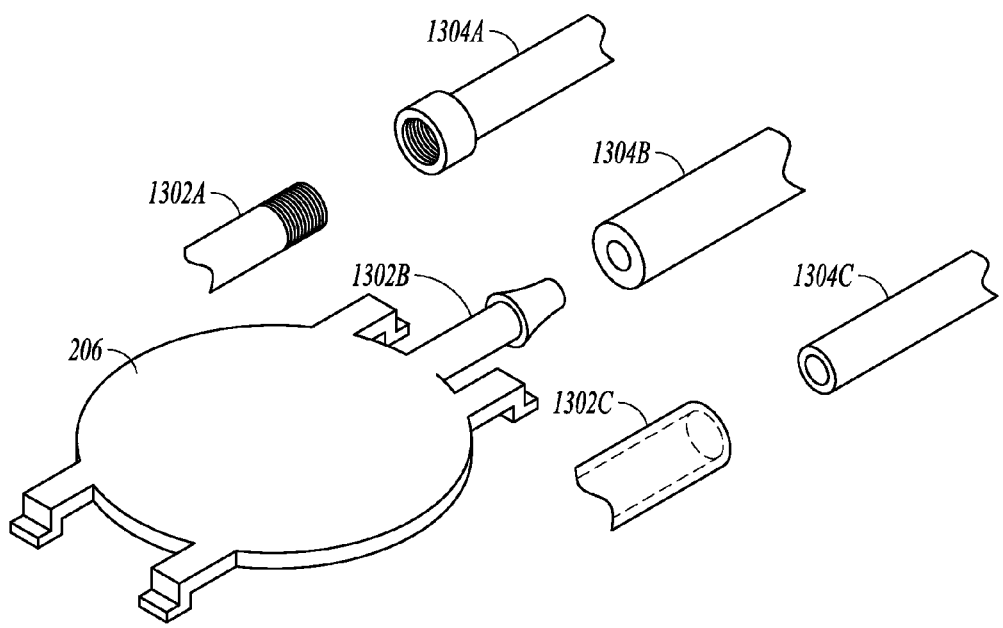
FIG. 13 shows an example that can include an optional infusion, drainage, or other port, such as can be located in or coupled to a cap.

FIG. 13 shows an example that can include an infusion, drainage, or other port 1302, such as can be located in or coupled to the cap 206. In an example, the port 1302 can exit the cap 206 laterally, such as to help permit overlying skin to be sutured partially or preferably completely closed, such as explained above. The port 1302 can include one or more features to allow it to be frictionally coupled to or otherwise engaged to or sealed against a catheter 1304 or the like, which can be coupled to the port 1302, such as to allow infusion or drainage. In an example, a port 1302A can include external or internal threads that can be configured to threadably engage corresponding internal or external threads of an end portion of the catheter 1304A. In an example a port 1302B can include a lip that can be configured to retain a compliant end portion of the catheter 1304B. In an example, a portion 1302C can include a female receptacle into which a distal end portion of the catheter 1304C can be inserted. Thus, the port 1302 can be configured to inhibit inadvertent pulling of the catheter 1304 away therefrom.

Portions of the system 100 or the trajectory guide apparatus 102 can be constructed of suitable biocompatible or MRI compatible materials. To recap, the system 100 and trajectory guide apparatus 102 can provide trajectory guidance for an diagnostic, therapeutic, or other interventional instrument, such as based on the user's knowledge of the subject's anatomy, which may be based on real-time or pre-operative magnetic resonance (MR), computed tomography (CT), or another imaging modality. Advantages of the present systems, devices, or methods can include, among other things, that the trajectory guide 102 can include cranial access port components—including the ball 106 and the retainer 108—which need not be removed, or even unsecured after the trajectory is aligned to prepare for introducing the instrument through the trajectory guide 102. This can help provide more accurate delivery of the instrument to the desired target. Moreover, the access port components of the trajectory guide apparatus 102 can be located substantially within the burr hole or can provide a low-profile so as to allow the skin to be sutured closed over such access port components of the trajectory guide apparatus 102. The guide stem 110 can be removed while leaving the instrument in place through the ball passage 107—even if the instrument includes a proximal bulge that is wider than the bore 111 of the guide stem 110 because, in an example, the guide stem 110 can be split into two or more sections, such as the sections 110A, 110B. Furthermore, it can maintain a cannula 502 or other conduit to the target, while providing for attachment thereto, such as by a flexible lateral catheter 702, which can be tunneled beneath the scalp. The cannula 502 can be used to deliver a substance to the target or to drain a substance from the target. Alternatively or additionally to the tunneled lateral catheter 702, the cap 206 can include a port, such as an injection port, such as to deliver a flowable substance (e.g., a drug or other infusate) to the target, such as through the cannula 502.

Fiducial Marker Arrangement Examples

Another aspect of the present systems, devices, and methods can include subject matter related to medical imaging, and more particularly, to localizing an interventional (e.g., diagnostic, therapeutic, or other) device within or around the body of a human or animal subject, such as by using a medical imaging system (e.g., MRI, fMRI, CT, PET, ultrasound, or another imaging modality).

The system 100 and trajectory guide 102 described above (as well as other trajectory guide devices that need not have the features or advantages of the trajectory guide 102 described above) can be used for delivering an interventional instrument to a desired area of the human or animal body, such as a desired target within the human or animal body. This can be done under guidance of a pre-operative or real-time imaging modality. For example, a typical MRI is capable of clearly imaging soft tissue and fluid within the bore of the MRI magnet.

One approach can be to visually align a trajectory, such as by using a tube filled with an imaging-recognizable fluid, such as saline or a combination of saline and gadolinium, which can enhance the imaging visibility of the fluid. In this approach, the tube can then be held concentrically within a bore of a guide stem of a trajectory guide, and the trajectory guide can then be visually aligned with the desired target. In this approach, the fluid-filled tube can then be removed and replaced with the instrument being delivered. The present inventors have recognized that in this approach, however, after the fluid-filled tube is removed from the guide stem of the trajectory guide, alignment can no longer be confirmed using the imaging modality.

Accordingly, the present inventors have recognized that another approach can be provided. At least three points or other objects can be used as user-visualizable or machine-imageable or other fiducial markers, such as to define a plane. If those points also define a geometric shape on that plane, such as, for example, a triangle (e.g., using at least 3 points), a rectangle (e.g., using at least 4 points), a pentagon (e.g., using at least 5 points), etc., such a centroid (a unique center of area) may be defined on that plane with respect to those fiducial marker points and the shape that they create. If such fiducial marker points are visible in an MRI or other imaging modality's image, they can define a unique axis that is (a) perpendicular to the plane and (b) intersecting the centroid. If such fiducial markers are arranged on the defined plane such that the fiducial markers themselves do not lie along such trajectory axis defined perpendicular to their shared common centroid, then such fiducial marker points can be left in place to allow imaging during instrument delivery without obstructing the trajectory path. This can allow for the delivery of an instrument while concurrently providing alignment confirmation using the imaging modality, whether MR, CT, or any other imaging modality in which the fiducial marker points can be made visible. Moreover, a "depth to target" can be measured, such as the distance from such centroid (or referenced thereto, such as from a proximal end of the guide stem 110) to the target along the trajectory axis. Furthermore, a second point along the trajectory axis can be defined as a virtual "probe-tip" or "pointer," such as to allow for localization of one or more points of interest within the image.

Figure 9A:
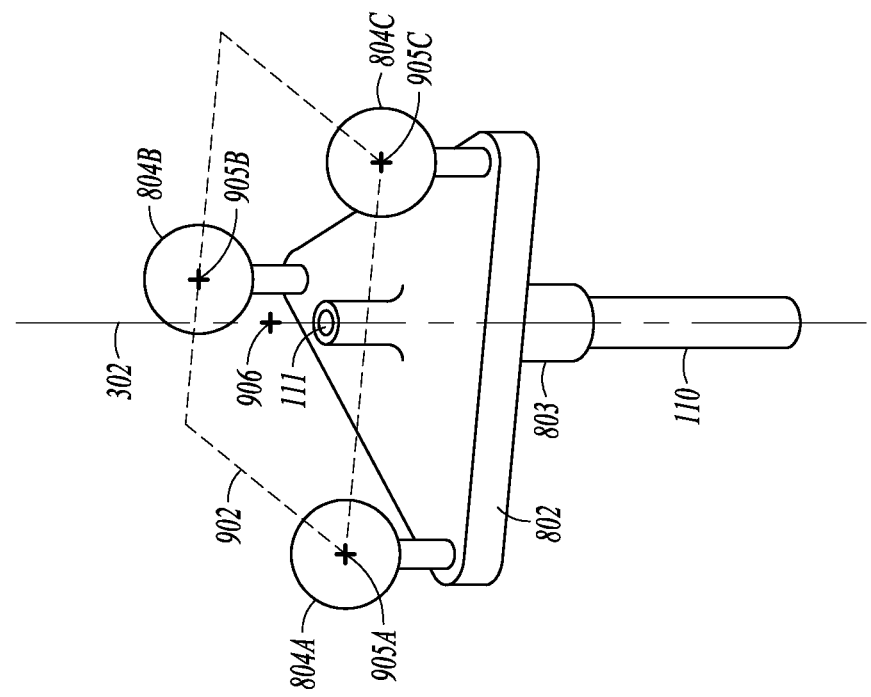
FIGS. 8 and 9A-9B respectively show an exploded view and an isometric view of an example of a platform or other structure that can be included in or used with the system and the trajectory guide, or with a different system or trajectory guide, or as an independent "alignment wand" without any other system or trajectory guide.
Figure 8:
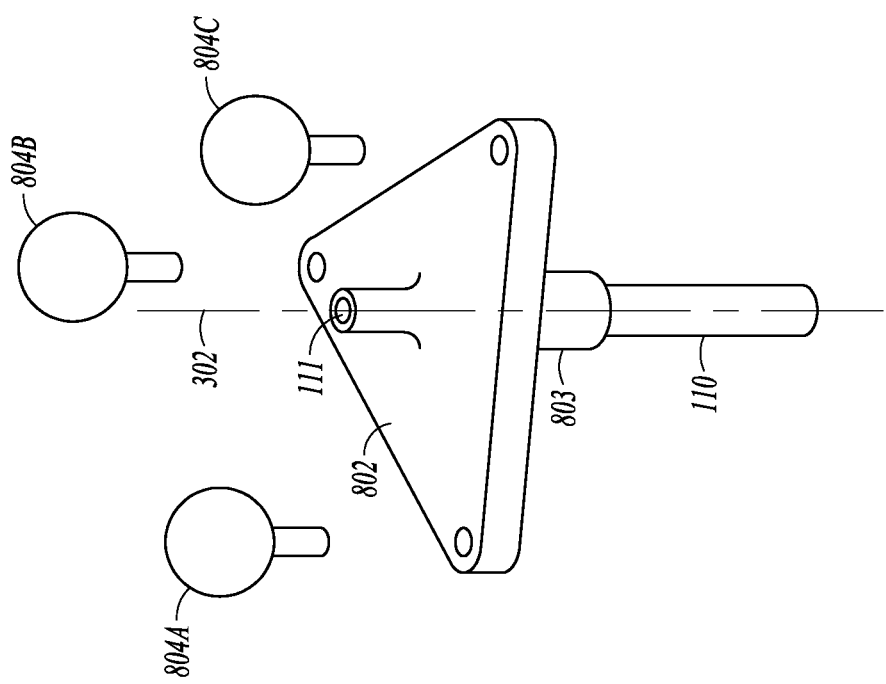
Figure 9B:
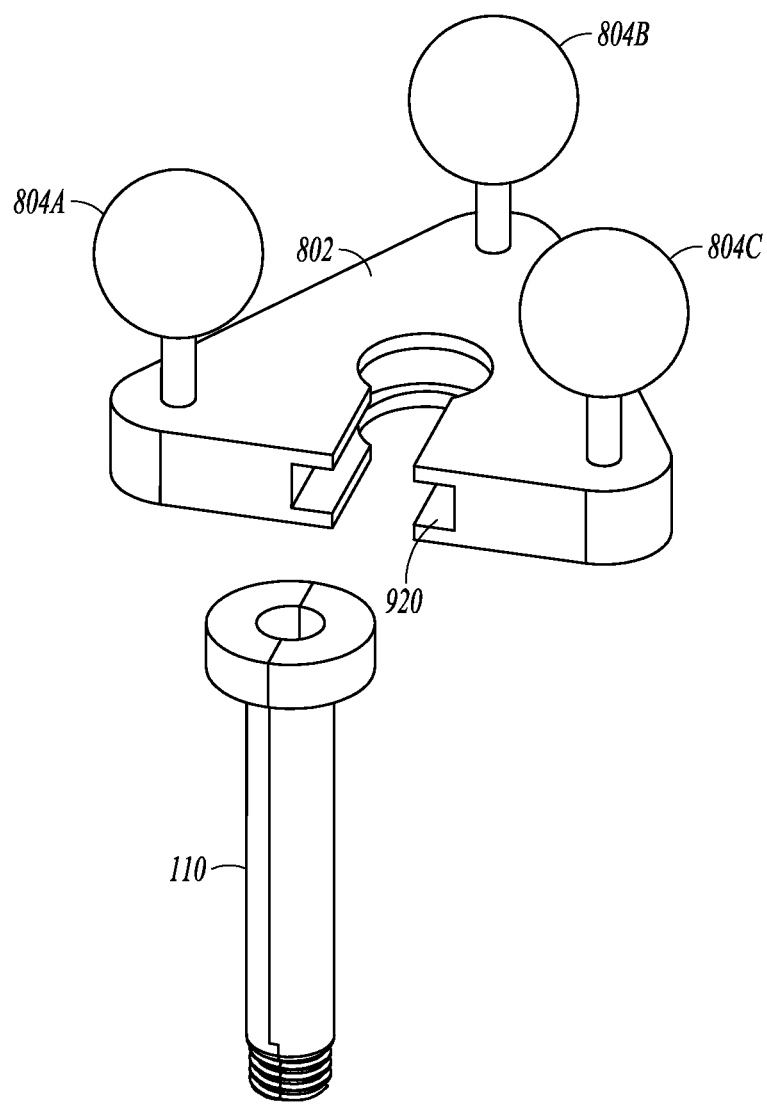

FIGS. 8-9A-B respectively show an exploded view and an isometric view of an example of a platform 802 or other structure that can be included in or used with the system 100 and the trajectory guide 102 described above (or with one or more other instruments or trajectory guide devices that need not have the features or advantages of the trajectory guide 102 described above). The platform 802 can be used to help performing imaging, such as for locating a desired area on a human or animal subject, such as for delivering an interventional instrument to a desired area of the human or animal body, such as to a desired target within the human or animal body. In an example, the platform 802 can be secured, affixed, or mounted to the guide stem 110 (or to an instrument to be passed through the bore 111 of the guide stem 110). The guide stem 110 can have two user-separable parts 110A-B, such as described above. The platform 802 can be secured such that the platform 802 does not obstruct the bore 111 of the guide stem 110, such as by allowing the bore 111 of the guide stem 110 to pass through the platform 802 in an example, or by allowing the bore 111 of the guide stem 110 to coaxially align with a corresponding bore portion of the platform 802 that effectively extends the bore 111 of the guide stem 110. For example, FIG. 9B shows an example in which a proximal portion of the guide stem 110 can be slid into a slot 920 in a side of the platform 802 such that the platform 802 can be centered upon the guide stem 110. This can effectively allow the bore 111 of the guide stem 110 to pass through the platform 802 or at least be unobstructed by the platform 802. This can permit the instrument 111 to still be passed through the bore 111 of the guide stem 110. In an example, the platform 802 can be affixed to the guide stem 110 by a hollow center post 803 portion of the platform 802. The post 803 can extend orthogonally from the platform 802 such that the post 803 can slip snugly over the guide stem 110.

An arrangement of one or more machine-imageable fiducial markers 804 can be located on the platform 802. The fiducial markers 804 can be placed at specified locations on the platform 802 such as to define a first plane 902 that is orthogonal to the longitudinal trajectory 302 defined concentrically to the bore 111 of the guide stem 110. In the example of FIG. 8, this can include three substantially spherical (or other centroid-defining) MRI-visible fluid-filled fiducial markers 804A-C, which can each define a respective concentric center 905A-C of the corresponding individual spherical fiducial marker 804A-C. The individual centroids 905A-C of the respective fiducial markers 804A-C can collectively define a specified or determinable common centroid 906 on the first plane 902, wherein the first plane 902 is orthogonal to the trajectory 302. In an example, the MR or other imaging modality being used can recognize the locations of the centroids 905A-C of the fiducial markers 804A-C, such as by using an image-processing circuit that coupled to the MR scanner. From these centroid locations 905A-C, the image-processing circuit can determine the orientation of their common first plane 902, and can compute the location of the common centroid 906 within the common first plane 902. The common centroid 906 within the common first plane 902 can be located at its intersection with the orthogonal trajectory 302, or in a specified relationship thereto, such as by appropriate selection of the physical locations of the fiducial markers 804A-C on the platform 802.

The platform 802 can include threaded receptacles into which respective posts extending from the spherical portions of the fiducial markers 804A-C have been threaded. Each post can be precisely configured with a threaded distal portion to be inserted to a specified depth. Accordingly, when the posts of the fiducial markers 804A-C are inserted into the platform 802, the first plane 902 defined by the respective centroids 905A-C of the fiducial markers 804A-C is orthogonal to the trajectory 302 through the bore 111 of the guide stem 110.

In the example of FIGS. 8-9, the common centroid 906, defined by the individual centroids 905A-C of the respective fiducial markers 804A-C, is located at the intersection between the first plane 902 and the orthogonal trajectory 302 extending through the bore 111 of the guide stem 110 over which the hollow post 803 has been fitted. However, in other examples, the common centroid 906, defined by the individual centroids 905A-C of the respective fiducial markers 804A-C, can be located in another (different) specified or determinable (e.g., by the image-processing circuit) location with respect to at the intersection between the first plane 902 and the orthogonal trajectory 302 extending through the bore 111 of the guide stem 110 over which the hollow post 803 has been fitted.

In a real-time MR imaging example, the platform 802 and the guide stem 110 or other components of the system 100 can be made of any suitable non-magnetic material, such as plastic, ceramic, carbon fiber, or the like. In a CT example, a metal or metal alloy, such as aluminum or stainless steel can be used, in addition or as an alternative to plastic, ceramic, carbon fiber or the like. In an example, the platform 802 can be integrally constructed as part of the guide stem 110. In an MR imaging example, the fluid-filled fiducial markers 804 can include a container material that can be made of plastic, glass, ceramic, or carbon fiber, which can be filled with an imageable fluid such as saline, gadolinium, a mix, or any medium that is visible in the imaging modality used.

While the example described above with respect to FIGS. 8-9 has particularly emphasized a specific device and method of aligning a trajectory 302 for introducing an instrument using MRI, these techniques can also be applied to CT or another imaging modality in which their locations can be made visible. Unlike an approach in which an imager-visible fluid-filled stem is inserted into the bore 111 of the guide stem 110, and then removed for allowing subsequent instrument insertion, the platform 802 and the fiducial markers 802A-C can be left in place during insertion of the cannula 502 or another instrument into the bore 111 of the guide stem 110, thereby allowing real-time imaging verification of the alignment even during instrument delivery.

While the example described above with respect to FIGS. 8-9 has particularly emphasized and illustrated the use of multiple (e.g., three) separate discrete fiducial markers 804A-C, other arrangements one or more fiducial markers can additionally or alternatively be used to define the first plane 902. For example, a single contiguous substantially flat ring-shaped fiducial marker can also be used to define the first plane 902, and can define a centroid within the first plane 902 that is at a specified or determinable location with respect to the orthogonal trajectory 302. Similarly, one or more other two dimensional (2D) or three dimensional (3D) shapes can be used to define a plane and a specified or determinable centroid in that plane—and can leave unobstructed the bore 111 of the guide stem 110, thereby allowing real-time imaging verification of the alignment of the trajectory 302, even during instrument delivery.

FIGS. 10A-10E show an example of using a single (e.g., ring-shaped) first fiducial marker 1000 arranged to define a first plane 902 that is orthogonal to the trajectory 302. A single (e.g., ring-shaped) second fiducial marker 1001 can be provided and arranged to define a second plane 1002 that is also orthogonal to the trajectory 302. The second plane 1002 is spaced-apart from the first plane 902 by a specified distance. The first plane 902 can be spaced-apart from the second plane 1002 by mounting, securing, or otherwise affixing the first and second fiducial markers 1000, 1001 to a connector beam 1004, which can serve as a tie or strut between the fiducial markers 1000, 1001. In an example, the guide stem 110 itself can serve as the connector beam 1004. In an example, the instrument to be inserted to the target 1008 via the bore 111 of the guide stem 110 along the trajectory 302 can serve as the connector column 1004.

In the example of FIGS. 10A-E, the ring fiducial markers 1000, 1001 can define respective centroids 1010A-B in the first plane 902 and the second plane 1002, respectively, such as at the respective intersections of these planes with the trajectory 302 passing orthogonally through each, or in a (preferably like, but possibly different) specified or determinable distance and relationship to the trajectory 302.

Figure 10B:
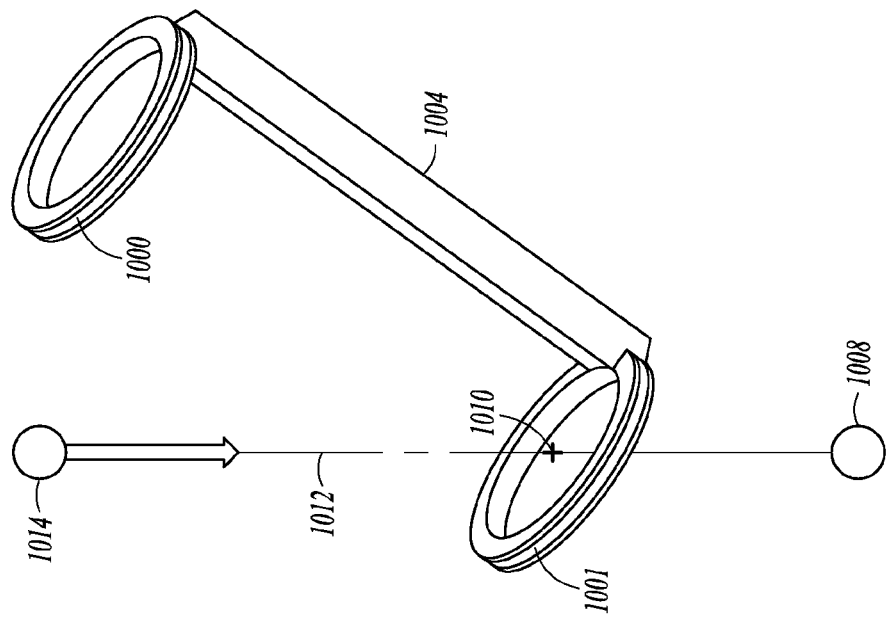
FIGS. 10A-10E show an example of using a single (e.g., ring-shaped) first fiducial marker arranged to define a first plane that is orthogonal to the trajectory, and a single (e.g., ring-shaped) second fiducial marker that can optionally be provided and arranged to define a second plane that is also orthogonal to the trajectory.
Figure 10A:
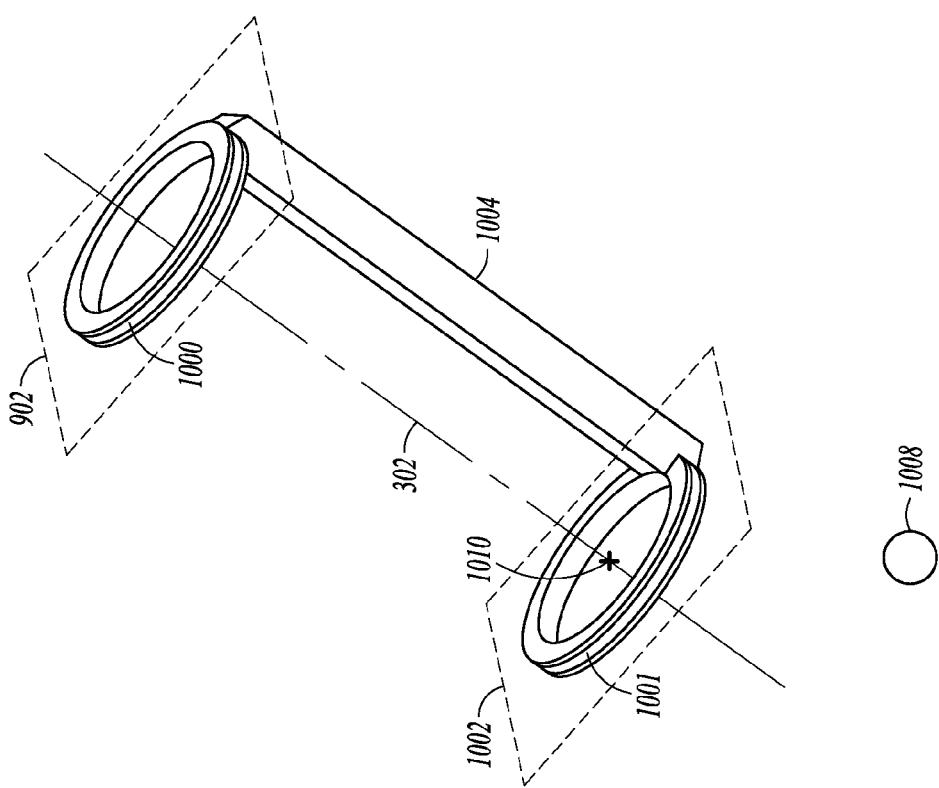

FIGS. 10A-10E show an example in which the ring fiducial markers 1000, 1001 can each be arranged to be concentric to the trajectory 302, each providing a respective centroid located at an intersection of the trajectory 302 through the respective planes defined by the rings of the fiducial markers 1000, 1001. In the example of FIG. 10A, the rings can have like diameters. In another example, however, the rings can have different diameters, for example, such that at least a portion of each is concurrently visible when looking directly down the trajectory 302.

FIG. 10A illustrates an example in which the fiducial markers 1000, 1001 can be arranged with respect to the trajectory guide apparatus 102 so as to pivot about a pivot point 1010 in the second plane 1002, such as a pivot point 1010 defined by the centroid of the fiducial marker 1001. The trajectory 302 passes through the pivot point 1010 orthogonal to the second plane 1002.

FIG. 10B illustrates an example of how, for example, using the imaging modality, a desired line 1012 can be constructed through a centroid of the target 1008 and through the pivot point 1010 defined by the centroid of the fiducial marker 1001. Using the imaging modality, in an example, a point 1014 can be selected along the desired line 1012 and above the ring fiducial marker 1000. In an example, selection of the point 1014 can be subjective, such as based on a visual estimation of the centroid of the target 1008, either using the imaging modality or using visualization without the imaging modality.

Figure 10C:
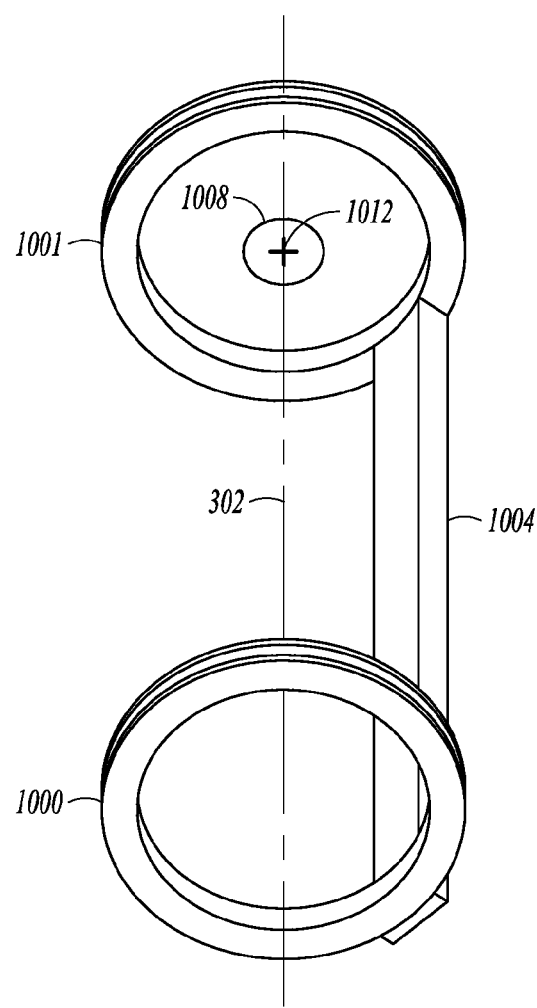

FIG. 10C illustrates an example of how, using the imaging modality to view axially down the desired line 1012, the ball 106 can be pivoted in the socket 120 such that the trajectory 302 aligns with the desired line 1012, thereby pointing the trajectory 302 toward the target 1008. In FIG. 10C, the desired line 1012 is perpendicular to the page of the drawing, and is not yet aligned to the trajectory 302.

Figure 10D:
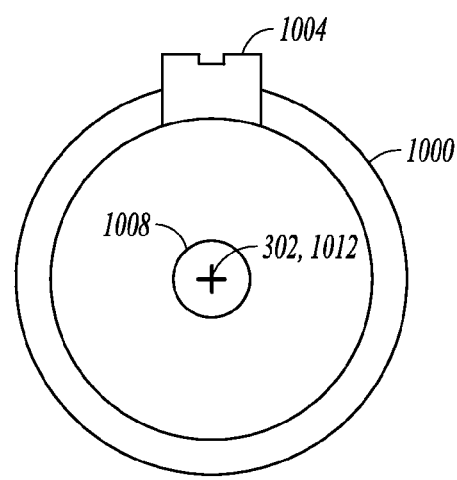

FIG. 10D shows how such alignment between the trajectory 302 and the desired line 1012 can be accomplished by aligning the ring fiducial markers 1000, 1001 until they visually align concentrically, such as when viewed with the imaging modality down along the desired line 1012. This can be conceptualized as sighting a target through two ring-shaped gun sights. The trajectory 302 is then aligned to the target 1008. This is shown in FIG. 10D, with both the desired line 1012 and the trajectory 302 being perpendicular to the page of the drawing. The ball 106 can then be secured, such as by using the retainer 108, as described above. The cannula 502 or another instrument can then be introduced along the trajectory 302 to the target 1008. Such alignment can be accomplished using the imaging modality, visually, or a combination thereof. Although FIG. 10D shows an example with like-diameter ring fiducial markers 1000, 1001, different-diameter ring fiducial markers 1000, 1001 can also be used.

Figure 10E:
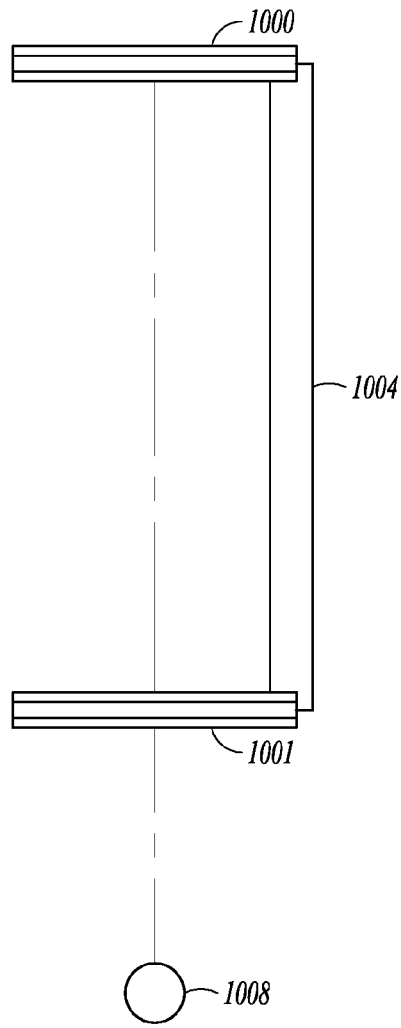

FIG. 10E shows how a depth-to-target measurement may be made, using the imaging modality, in an orthogonal view to the trajectory 302. One or more of the rings of the fiducial markers 1000, 1001 can be arranged in a specified or determinable spatial relationship to a reference point at which the instrument is to be inserted. In this way, such a ring can be used as a reference for the depth-to-target measurement, which can be made in the orthogonal view using the imaging modality.

With respect to the examples shown in FIGS. 10A-10E, in other examples, there can be more than two ring or other fiducial markers 1000, 1001 provided, such as to provide additional corresponding planes that are orthogonal to the trajectory 302. Moreover, the fiducial markers 1000, 1001 need not have ring shapes—other symmetrical shapes or other shapes, from which a centroid can be determined (e.g., without the shape blocking the bore 111 of the instrument guide 110), can also be used. Such shapes need not be a single continuous shape, like a ring. For example, multiple discrete shapes, such as the spherical fiducial markers 804A-C described above, can also be used to define a plane and a common centroid within that plane. In an example, the fiducial markers 1000, 1001 can be auto-detected by software, such as can be performed on the image-processing circuit that is included in or coupled to the imaging modality. Enhanced visibility using the imaging modality can be facilitated using fluid, metal, or other MR or radio-opaque materials, as appropriate for the particular imaging modality selected.

The above description of the various fiducial marker structures has emphasized how they can be included in or used with the systems and the trajectory guides described herein. However, such fiducial marker structures and methods can also be used with other systems or trajectory guides, or even without an accompanying trajectory guide, such as an independent "alignment wand" that can be used with an imaging modality or other machine-assisted visualization system.

Figure 14:
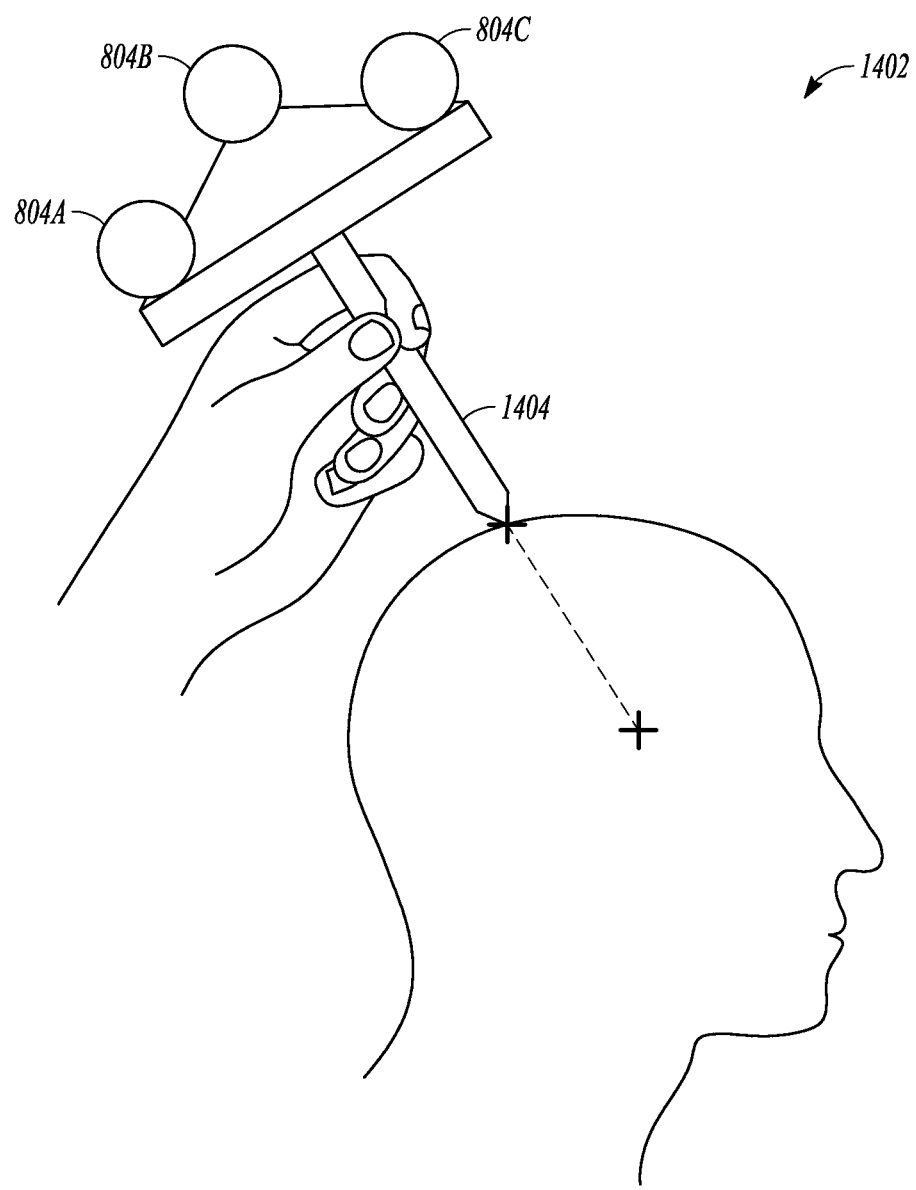
FIG. 14 shows an example of such an alignment wand that can incorporate one or more of the features of the various fiducial marker arrangements described above, without requiring integration with a trajectory guide.

FIG. 14 shows an example of such an alignment wand 1402 that can incorporate one or more of the features of the various fiducial marker arrangements described above, without requiring integration with a trajectory guide, but allowing for use with or without such a trajectory guide, as desired. In an example, the alignment wand 1402 can include a post 1404, which can optionally be configured to be inserted smoothly and snugly into the bore 111 of the guide stem 110. Regardless of whether it is inserted into the guide stem 110, the post 1404 can define a planned instrument trajectory 302, and can include an arrangement of fiducial markers 804A-C arranged on a platform 802 to define a plane orthogonal to the trajectory 302, such as described above, for example, with respect to FIG. 8.

Figure 15A:
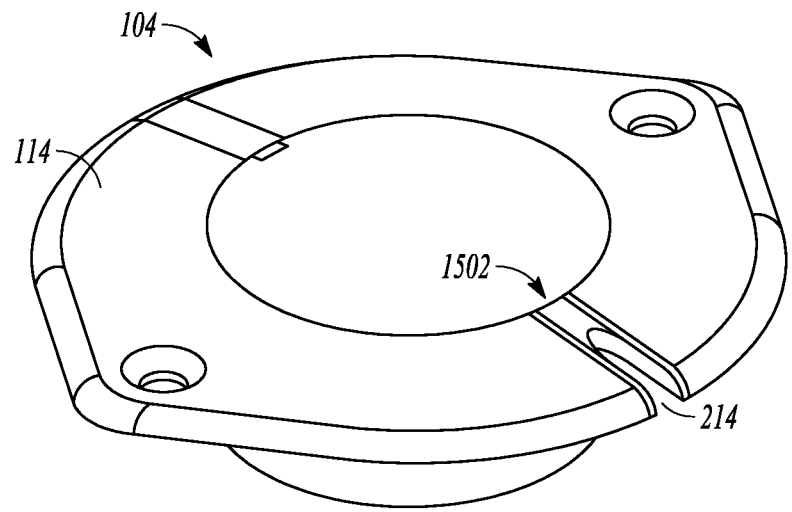
FIGS. 15A, 15B, and 15C show various views of an example of a base with a detent or restraint, such as a biocompatible clip.
Figure 15B:
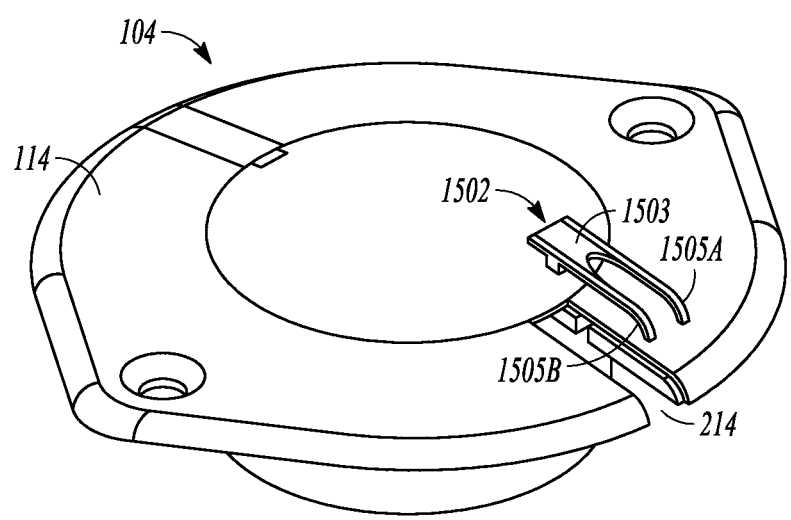
Figure 15C:
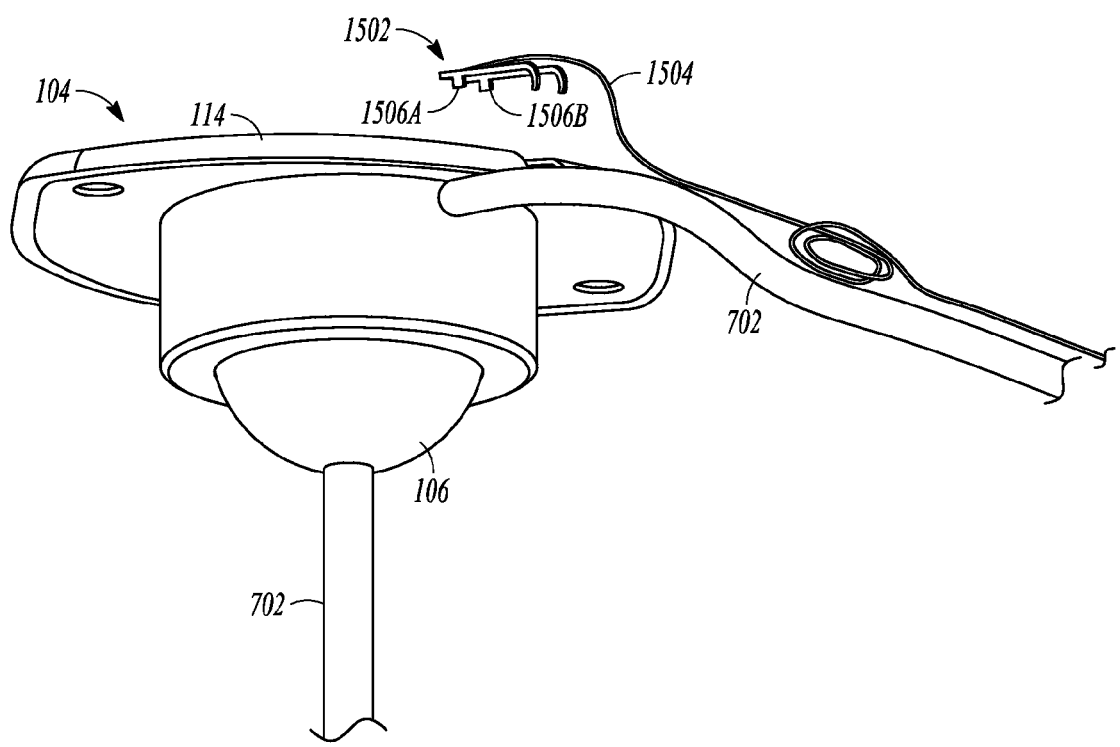

FIGS. 15A, 15B, and 15C show various views of an example of the base 104 in which at least one of: (1) the instrument exit portal 212 (in the cap 206); or (2) the instrument exit portal 214 (extending laterally across the flange 114), can optionally include a user-attachable, user-detachable, or user-attachable and user-detachable detent or restraint, such as a biocompatible clip 1502. The clip 1502 can be sized, shaped, or otherwise configured to help constrain or secure an instrument, such as a lead or catheter 702. The clip 1502 can provide an interference fit about the lead or catheter 702, such as to more securely anchor the lead or catheter 702 at the instrument exit portal 214.

In an illustrative example, the clip 1502 can include a trunk portion 1503, such as in a medial direction toward the center of the base 104. From the trunk portion 1503, a pair of legs 1505A-B can extend outward, such as in a lateral direction out from the center of the base 104. The clip 1502 can include one or more snap-fit or other engagement features 1506, such as can be located at opposing sides of the trunk portion 1503. The one or more engagement features 1506 can engage corresponding one or more mating or reciprocal snap-fit or other engagement features in the base 104 or the cap 206. The clip 1502 can fit within the instrument exit portal 212, 214 of the base 104 or the cap 206, such as flush to a face of a corresponding one thereof. In an example, such inserting of the clip 1502 into an instrument exit portal 212, 214 can push the legs 1505A-B toward each other, such as to compressively secure therebetween the lead or catheter 702 or other such instrument.

In an example, once the lead or catheter 702 is implanted, before the cap 206 is placed upon the base 104, the clip 1502 can be snap-fitted into one of the instrument exit portals 212, 214. Using the clip 1502 can permit the other passageways (e.g., the instrument exit portals 212, 214) to be larger, more gentle, or more forgiving. In this way, when the clip 1502 is not present, the lead or catheter 702 can be more easily removed by pulling it out. Such pulling can involve the user exerting a pulling force on a more proximal location of the lead or catheter 702, e.g., away from the clip 1502.

A tether 1504 optionally can be attached to the clip 1502. The tether 1504 can be routed subcutaneously, along with the lead or catheter 702, for a desired distance or to a desired location. Beyond this desired subcutaneous routing distance, the lead or catheter 702 can emerge proximally out from under the skin, such as together with a proximal portion of the tether 1504. By pulling on an exposed proximal portion of the tether 1504, a user can use the tether 1504 as a "ripcord," such as to remotely release the clip 1502 from the base 104 or the cap 206. Such releasing of the clip 1502 from the base 104 or the cap 206 can allow the lead or catheter 702 to move freely at the instrument exit portals 212, 214, which can allow convenient user extraction or removal of the lead or catheter 702 by pulling on the proximal end of the tether 1504.

The tether 1504 can optionally include a coiled or slack portion between the clip 1502 and the proximal end of the tether 1504, such as at a subcutaneous location, if desired. This can help guard against accidental release of the clip 1502, e.g., by an accidental minor tug on the tether 1504 that does not exceed a pull distance needed to release the slack in the tether 1504. In an example, the tether 1504 can be omitted, and the lead or catheter 702 can itself be used by the user as a ripcord to release the clip 1502 from the base 104, such as by suturing, clipping, or otherwise affixing the clip 1502 to the lead or catheter 702, such as at the instrument exit portal 212, 214.

Additional Notes & Examples

Example 1 can include subject matter (such as an apparatus, a method, a means for performing acts, or a machine-readable medium including instructions that, when performed by the machine, cause the machine to perform acts) that can include or can use a trajectory guide apparatus. The trajectory guide apparatus can include a base, configured to be able to be capable of being affixed substantially in a burr hole in a human or animal subject, the base including a socket configured to be located in the burr hole when the base is affixed to the subject. The trajectory guide apparatus can include a spherical or other ball, configured to be located in and pivotable with respect to the socket and to be located substantially in the burr hole when the base is affixed to the subject, the ball including therethrough a pivotably adjustable instrument guide ball passage providing an adjustable instrument trajectory defined longitudinally by the ball passage. The trajectory guide apparatus can include an engageable ball retainer, configured to be located substantially within the burr hole when engagably coupled to the base that is located substantially within the burr hole, the retainer configured to secure the ball to inhibit pivoting of the ball to hold the instrument trajectory substantially constant.

Example 2 can include or use, or can optionally be combined with the subject matter of Example 1 to include or use an elongate guide stem, including a proximal end and a distal end and a bore therebetween, wherein the distal end of the guide stem is configured to engageably concentrically align the bore with the ball passage, such that the guide stem extends longitudinally outward from and supported by the ball. The guide stem can include sections capable of being user-separated from each other when an instrument is in the bore and the ball passage such that the instrument remains within the ball passage without being constrained by the bore after the user-separation of the guide stem sections.

Example 3 can include or use, or can optionally be combined with the subject matter of one or any combination of Examples 1-2, such that the guide stem can include an outer threaded portion, the ball passage can include an inner threaded portion, and the outer threaded portion of the guide stem can be configured to threadably engage the inner threaded portion of the ball passage, and comprising a thread cover, having an outer circumferential surface and a smooth inner circumferential surface.

Example 4 can include or use, or can optionally be combined with the subject matter of one or any combination of Examples 1-3 to include or use a platform that can be user-attachable to or user-detachable from the proximal end of the elongate guide stem. The platform can include a first set of one or more fiducial markers, disposed in and commonly defining a first plane extending orthogonal to the trajectory. The platform can include a passage configured to allow the instrument trajectory therethrough.

Example 5 can include or use, or can optionally be combined with the subject matter of one or any combination of Examples 1-4 to include or use a flange, such as included in or coupled to the base, the flange can be configured to extend at least partially about the burr hole so as to locate the base substantially within the burr hole so as to be capable of allowing overlying skin to be sutured closed.

Example 6 can include or use, or can optionally be combined with the subject matter of one or any combination of Examples 1-5, such that the retainer can include an outer thread that can be configured to threadably engage an inner thread of at least one of the base or a flange that can be included in or coupled to the base. An engageable feature can allow rotatable threading of the retainer into at least one of the base or the flange. The engageable feature need not substantially protrude above a top surface defined by the base or the flange.

Example 7 can include or use, or can optionally be combined with the subject matter of one or any combination of Examples 1-6, such that the retainer can include a ring. The ring can be configured to be seated upon the ball and can be configured to secure the ball to inhibit pivoting of the ball to hold the instrument trajectory substantially constant. The ring can include at least one of a hinge or a snap-in engageable feature.

Example 8 can include or use, or can optionally be combined with the subject matter of one or any combination of Examples 1-7, to include or use an instrument hub. The instrument hub can be configured to be located between and to frictionally engage an instrument in the ball passage and an inner wall of the ball passage.

Example 9 can include or use, or can optionally be combined with the subject matter of one or any combination of Examples 1-8 to include or use a longitudinal lumen, which can extend longitudinally in the ball passage. A lateral lumen can exit laterally from the base at a lumen constraint portion of the base.

Example 10 can include or use, or can optionally be combined with the subject matter of one or any combination of Examples 1-9 to include or use a cap, which can be configured to substantially cover the base to retain fluid in the base in a reservoir under the cap. The cap can include an injection port configured for injecting fluid into the reservoir.

Example 11 can include or use, or can optionally be combined with the subject matter of one or any combination of Examples 1-10 to include or use a first set of one or more fiducial markers, such as disposed in and commonly defining a first plane extending orthogonal to the trajectory.

Example 12 can include or use, or can optionally be combined with the subject matter of one or any combination of Examples 1-11 such that the first set of one of more fiducial markers defines a centroid at a location in the first plane that is in a specified or determinable relationship to a location where the first plane is intersected by the trajectory.

Example 13 can include or use, or can optionally be combined with the subject matter of one or any combination of Examples 1-12 such that the first set of one or more fiducial markers defines a centroid at the location where the first plane is intersected by the trajectory.

Example 14 can include or use, or can optionally be combined with the subject matter of one or any combination of Examples 1-13 to include or use a second set of one or more fiducial markers, disposed in and commonly defining a second plane extending orthogonal to the trajectory and spaced apart from the first plane.

Example 15 can include or use, or can optionally be combined with the subject matter of one or any combination of Examples 1-14 such that the first and second sets of fiducial markers can respectively include spaced-apart rings that are each concentric to the trajectory.

Example 16 can include or use, or can optionally be combined with the subject matter of one or any combination of Examples 1-15 such that the first set of fiducial markers defines a centroid at the intersection of the first plane and the trajectory, and wherein the second set of fiducial markers defines a centroid at the intersection of the second plane and the trajectory.

Example 17 can include or use, or can optionally be combined with the subject matter of one or any combination of Examples 1-16 to include or use a trajectory guide apparatus that has previously been affixed to a subject such that a base of the trajectory guide is affixed substantially in a burr hole in a human or animal subject. This can include pivoting a spherical or other ball, located in a socket portion of the base that is located in the burr hole, to align a longitudinal trajectory of an instrument guide ball passage through the ball to a desired target. This can also include securing the ball, to hold the aligned trajectory substantially constant, using a ball retainer that is located substantially within and engageably coupled with the base.

Example 18 can include or use, or can optionally be combined with the subject matter of one or any combination of Examples 1-17 such that securing the ball can include threading the retainer into the base using an engageable feature of the retainer that does not substantially protrude above a top surface of the flange.

Example 19 can include or use, or can optionally be combined with the subject matter of one or any combination of Examples 1-18 to include or use inserting an instrument through the ball passage and a bore of an elongate guide stem engaged to the ball with the bore aligned with the ball passage. This can also include disengaging the guide stem from the ball with the instrument still passed through the bore and the ball passage. This can also include separating the guide stem into sections to remove the guide stem, such that the instrument remains within the ball passage without being constrained by the bore.

Example 20 can include or use, or can optionally be combined with the subject matter of one or any combination of Examples 1-19 to include or use, after disengaging the guide stem from the ball, covering threads in the ball passage with a spacer to inhibit the instrument from rubbing against the threads in the ball passage.

Example 21 can include or use, or can optionally be combined with the subject matter of one or any combination of Examples 1-20 to include or use frictionally engaging the instrument within the ball passage, without deforming the ball passage.

Example 22 can include or use, or can optionally be combined with the subject matter of one or any combination of Examples 1-21 to include or use providing a longitudinal lumen held longitudinally in the ball passage and a lateral lumen exiting laterally from the base.

Example 23 can include or use, or can optionally be combined with the subject matter of one or any combination of Examples 1-22 to include or use providing a fluid-retaining cap covering at least a portion of the base, and injecting fluid through an infusion port in the cap to a reservoir below the cap.

Example 24 can include or use, or can optionally be combined with the subject matter of one or any combination of Examples 1-23 to include or use aligning the trajectory to a desired target using a first set of one or more fiducial markers, disposed in and commonly defining a first plane extending orthogonal to the trajectory.

Example 25 can include or use, or can optionally be combined with the subject matter of one or any combination of Examples 1-24 to include or use aligning the trajectory to a desired target using a first set of one or more fiducial markers, disposed in and commonly defining a first plane extending orthogonal to the trajectory and defining a centroid in the first plane in a specified or determinable location with respect to the trajectory.

Example 26 can include or use, or can optionally be combined with the subject matter of one or any combination of Examples 1-25 to include or use aligning the trajectory to a desired target using a first set of one or more fiducial markers, disposed in and commonly defining a first plane extending orthogonal to the trajectory and defining a centroid in the first plane at a location where the first plane is intersected by the trajectory.

Example 27 can include or use, or can optionally be combined with the subject matter of one or any combination of Examples 1-26 to include or use aligning the trajectory to a desired target using a second set of one or more fiducial markers, disposed in and commonly defining a second plane extending orthogonal to the trajectory and spaced apart from the first plane, and defining a centroid in the second plane where the second plane is intersected by the trajectory.

Example 28 can include or use, or can optionally be combined with the subject matter of one or any combination of Examples 1-27 to include or use aligning the trajectory to a desired target using the first and second sets of fiducial markers that respectively include spaced-apart rings that are each concentric to the trajectory, by aligning the rings to each other when viewed along the trajectory and when the trajectory passes through the desired target.

Example 29 can include or use, or can optionally be combined with the subject matter of one or any combination of Examples 1-28 to include or use, subject matter (such as an apparatus, a method, a means for performing acts, or a machine-readable medium including instructions that, when performed by the machine, cause the machine to perform acts) that can include or can use a trajectory guide apparatus.

The trajectory guide apparatus can include a base, configured to be able to be capable of being affixed substantially in a burr hole in a human or animal subject, the base including a socket configured to be located in the burr hole when the base is affixed to the subject. The trajectory guide apparatus can include a spherical or other ball, configured to be located in and pivotable with respect to the socket and to be located substantially in the burr hole when the base is affixed to the subject, the ball including therethrough a pivotably adjustable instrument guide ball passage providing an adjustable instrument trajectory defined longitudinally by the ball passage. The trajectory guide apparatus can include an engageable ball retainer, configured to be located substantially within the burr hole when engagably coupled to the base that is located substantially within the burr hole, the retainer configured to secure the ball to inhibit pivoting of the ball to hold the instrument trajectory substantially constant. The retainer can include a ring. The ring can be configured to be seated upon the ball and can be configured to secure the ball to inhibit pivoting of the ball to hold the instrument trajectory substantially constant. The ring can include at least one of a hinge or a snap-in engageable feature, such as can be located on an internal perimeter of the ring. The ring can include an outer thread on its outer circumferential or other perimeter. The outer thread can be configured to threadably engage an inner thread of an inner circumference or other inner perimeter of at least one of the base or of a flange that can be included in or coupled to the base. The engageable feature can allow rotatable threading of the outer circumference or other outer periphery of the ring into the inner circumference or inner periphery of at least one of the base or of the flange.

Example 30 can include or use, or can optionally be combined with the subject matter of one or any combination of Examples 1-29 to include or use a user-detachable detent, retainer, clip, or the like to inhibit or prevent movement of an instrument with respect to an instrument exit slot of the base or of the cap.

Example 31 can include or use, or can optionally be combined with the subject matter of one or any combination of Examples 1-30 to include a tether, such as can be secured to the user-detachable detent, retainer, clip, or the like, such as for use as a ripcord to release the detent, retainer, clip, or the like from at least one of the base or the cap.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A trajectory guide apparatus, comprising:
   a base, configured to be able to be capable of being affixed substantially in a burr hole in a skull in a human or animal subject, the base including a socket configured to be located in the burr hole when the base is affixed to the skull of the subject;
   a spherical or other ball, configured to be located in and pivotable with respect to the socket and to be located substantially in the burr hole when the base is affixed to the subject, such that a central pivot point of the ball is located below a surface of the skull when the base is affixed to the skull of the subject, the ball including therethrough a pivotably adjustable instrument guide ball passage providing an adjustable instrument trajectory defined longitudinally by the ball passage;

an engageable ball retainer, configured to be located in and engageable into the socket, and to be contained substantially within the burr hole when the base is affixed to the subject and when the retainer is engaged into the socket of the base that is located substantially within the burr hole, the retainer engaged into the socket to secure the ball to inhibit pivoting of the ball to hold the instrument trajectory substantially constant, the retainer including a plurality of upward-facing user-engageable receptacle features to engage the retainer from above the burr hole to permit threading the retainer into the socket of the base such that the plurality of user-engageable receptacle features is contained within the socket of the base; and an elongate guide stem, including a proximal end and a distal end and a bore therebetween, wherein the distal end of the guide stem is configured to engageably concentrically align the bore with the ball passage, such that the guide stem extends longitudinally outward from and supported by the ball.

2. The apparatus of claim 1, comprising:
a flange, included in or coupled to the base, the flange configured to extend at least partially about the burr hole so as to locate the base substantially within the burr hole so as to be capable of allowing overlying skin to be sutured closed; and
wherein the retainer further includes a thread arranged to threadably engage the retainer into the socket and wherein the user-engageable feature of the retainer does not substantially protrude above a top surface defined by the base or the flange when the retainer is fully threaded into the socket to secure the ball.

3. The apparatus of claim 2, comprising a cap, configured to substantially cover the base, when the retainer is fully threaded into the socket to secure the ball, so as to be capable of allowing overlying skin to be sutured closed.

4. The apparatus of claim 3, wherein the cap includes an injection port configured to permit injecting fluid into a reservoir under the cap.

5. The apparatus of claim 2, comprising a clip that is sized and shaped to fit into a portion of the flange and to accept and securely retain a portion of a elongate medical device that is located at the flange.

6. The apparatus of claim 5, comprising a tether arranged to be coupled to the clip to permit release of the clip from the flange via the tether.

7. The apparatus of claim 5, wherein the clip includes:
a snap-fit feature that is sized and shaped to snap into engagement with the flange; and
a pair of arms that are spaced apart and spreadable to accept the portion of the elongate medical device therebetween such that the portion of the elongate medical device is securely retained by the pair of arms when the clip is snapped into engagement with the flange.

8. The apparatus of claim 1, wherein the ball passage includes an internally threaded portion, and wherein the distal end of the guide stem includes an externally threaded portion configured to thread into engagement with the internally threaded portion of the ball passage to concentrically align the bore with the ball passage, such that the guide stem extends longitudinally outward from and supported by the ball; and
wherein the guide stem includes sections that are configured to be capable of being user-separated from each other when an instrument is in the bore and the ball passage such that the instrument remains within the ball passage without being constrained by the bore after the user-separation of the guide stem sections, wherein the sections of the guide stem include user-separable externally threaded portions that are configured to thread into engagement with the internally threaded portion of the ball passage before the guide stem is separated into the sections.

9. The apparatus of claim 1, comprising:
a first set of one or more fiducial markers, disposed in and commonly defining a unique first plane extending orthogonal to the trajectory;
wherein the first set of one or more fiducial markers defines a centroid at a location in the first plane that is in a specified or determinable relationship to a location where the first plane is intersected by the trajectory; and
a second set of one or more fiducial markers, disposed in and commonly defining a unique second plane extending orthogonal to the trajectory and spaced apart from the first plane.

10. The apparatus of claim 9, wherein the first and second sets of fiducial markers respectively include spaced-apart rings that are each concentric to the trajectory.

11. The apparatus of claim 1, wherein the plurality of user-engageable receptacle features to externally engage the retainer from above the burr hole to permit threading the retainer into the socket of the base includes a retainer ring that is sized and shaped to be seated upon the ball.

12. A trajectory guide apparatus, comprising:
a base, configured to be able to be capable of being affixed to a skull of a human or animal subject;
an adjustable member, providing an adjustable instrument trajectory relative to the base;
a first set of one or more fiducial markers, disposed in and commonly defining a unique first plane extending orthogonal to the trajectory;
wherein the first set of one or more fiducial markers defines a centroid at a location in the first plane that is in a specified or determinable relationship to a location where the first plane is intersected by the trajectory; and
a second set of one or more fiducial markers, disposed in and commonly defining a unique second plane extending orthogonal to the trajectory and spaced apart from the first plane.

13. The apparatus of claim 12, wherein the first and second sets of fiducial markers respectively include spaced-apart rings that are each concentric to the trajectory.

14. The apparatus of claim 12, wherein the adjustable member includes a spherical or other ball, configured to be located in and pivotable with respect to the socket and to be located substantially in the burr hole when the base is affixed to the subject, such that a central pivot point of the ball is located below a surface of the skull when the base is affixed to the skull of the subject, the ball including therethrough a pivotably adjustable instrument guide ball passage providing an adjustable instrument trajectory defined longitudinally by the ball passage, and wherein the apparatus comprises:
an engageable ball retainer, configured to be located in and engageable into to the socket, and to be located substantially in the burr hole when the base is affixed to the subject and when the retainer is engaged into the socket of the base that is located substantially within the burr hole, the retainer engageable into the socket to secure the ball to inhibit pivoting of the ball to hold the instrument trajectory substantially constant, the retainer including at least one user-engageable feature to engage the retainer to permit engaging into the socket of the base; and an elongate guide stem, including a proximal end and a distal end and a bore therebetween, wherein the distal end of the guide stem is configured to engageably concentrically align the bore with the ball passage, such that the guide stem extends longitudinally outward from and supported by the ball.

15. The apparatus of claim 14, wherein the ball passage includes an internally threaded portion, and wherein the distal end of the guide stem includes an externally threaded portion configured to thread into engagement with the internally threaded portion of the ball passage to concentrically align the bore with the ball passage, such that the guide stem extends longitudinally outward from and supported by the ball; and wherein the guide stem includes sections that are configured to be capable of being user-separated from each other when an instrument is in the bore and the ball passage such that the instrument remains within the ball passage without being constrained by the bore after the user-separation of the guide stem sections, wherein the sections of the guide stem include user-separable externally threaded portions that are configured to thread into engagement with the internally threaded portion of the ball passage before the guide stem is separated into the sections.

16. A method comprising providing or using trajectory guide apparatus, the providing or using a trajectory guide apparatus comprising:

affixing a base substantially in a burr hole in a skull in a human or animal subject, the base including a socket configured to be located in the burr hole when the base is affixed to the skull of the subject;

locating a spherical or other ball pivotable with respect to the socket and contained substantially within the burr hole when the base is affixed to the subject, such that a central pivot point of the ball is located below a surface of the skull when the base is affixed to the skull of the subject, the ball including therethrough a pivotably adjustable instrument guide ball passage providing an adjustable instrument trajectory defined longitudinally by the ball passage;

engaging an engageable ball retainer, configured to be located in and engageable into to the socket, and to be located substantially in the burr hole when the base is affixed to the subject and when the retainer is engaged into the socket of the base that is located substantially within the burr hole, the retainer engaged into the socket to secure the ball to inhibit pivoting of the ball to hold the instrument trajectory substantially constant, the retainer including a plurality of upward-facing user-engageable receptacle features to engage the retainer from above the burr hole to permit threading the retainer into the socket of the base such that the plurality of user-engageable receptacle features is contained within the socket of the base; and using an elongate guide stem, including a proximal end and a distal end and a bore therebetween, wherein the distal end of the guide stem is used to engageably concentrically align the bore with the ball passage, such that the guide stem extends longitudinally outward from and supported by the ball.

17. The method of claim 16, comprising:

pivoting the spherical or other ball, located in a socket portion of the base that is located in the burr hole, to align a longitudinal trajectory of an instrument guide ball passage through the ball to a desired target; and securing the ball, to hold the aligned trajectory substantially constant, using the ball retainer that is located substantially within and engageably coupled with the base, by threading the ball retainer into the socket of the base.

18. The method of claim 16, comprising:

inserting an instrument through the ball passage and a bore of an elongate guide stem engaged to the ball with the bore aligned with the ball passage;

disengaging the guide stem from the ball with the instrument still passed through the bore and the ball passage; and separating the guide stem into sections to remove the guide stem, such that the instrument remains within the ball passage without being constrained by the bore.

19. The method of claim 16, comprising using a fluid-retaining cap for covering at least a portion of the base, and injecting fluid through an infusion port in the cap to a reservoir below the cap.

20. The method of claim 16, comprising:

aligning the trajectory to a desired target using a first set of one or more fiducial markers, disposed in and commonly defining a first plane extending orthogonal to the trajectory and defining a centroid in the first plane at a location where the first plane is intersected by the trajectory; and aligning the trajectory to a desired target using a second set of one or more fiducial markers, disposed in and commonly defining a second plane extending orthogonal to the trajectory and spaced apart from the first plane, and defining a centroid in the second plane where the second plane is intersected by the trajectory.

21. The method of claim 20, comprising aligning the trajectory to a desired target using the first and second sets of fiducial markers that respectively include spaced-apart rings that are each concentric to the trajectory, by aligning the rings to each other when viewed along the trajectory and when the trajectory passes through the desired target.

* * * * *